(12) United States Patent
Williams

(10) Patent No.: US 10,524,798 B2
(45) Date of Patent: *Jan. 7, 2020

(54) ANVIL ASSEMBLY DELIVERY SYSTEM

(71) Applicant: Covidien LP, Mansfield, MA (US)

(72) Inventor: Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 295 days.

This patent is subject to a terminal disclaimer.

(21) Appl. No.: 15/593,420

(22) Filed: May 12, 2017

(65) Prior Publication Data

US 2017/0245860 A1 Aug. 31, 2017

Related U.S. Application Data

(63) Continuation of application No. 14/263,412, filed on Apr. 28, 2014, now Pat. No. 9,655,626.

(51) Int. Cl.
| | |
|---|---|
| A61B 17/115 | (2006.01) |
| A61B 17/072 | (2006.01) |
| A61B 90/00 | (2016.01) |
| A61B 17/00 | (2006.01) |

(52) U.S. Cl.
CPC ........ A61B 17/1155 (2013.01); A61B 17/072 (2013.01); *A61B 2017/00477* (2013.01); *A61B 2017/07257* (2013.01); *A61B 2017/07278* (2013.01); *A61B 2090/0811* (2016.02)

(58) Field of Classification Search
CPC .. A61B 17/1155; A61B 17/072; A61B 17/068
USPC .......................... 227/177.1, 179.1, 180.1, 19
See application file for complete search history.

(56) References Cited

U.S. PATENT DOCUMENTS

| | | |
|---|---|---|
| 4,195,624 A | 4/1980 | Douglas |
| 4,263,914 A | 4/1981 | Pawlak |
| 4,304,236 A | 12/1981 | Conta et al. |
| 4,319,576 A | 3/1982 | Rothfuss |
| 4,328,805 A | 5/1982 | Akopov et al. |
| 4,379,457 A | 4/1983 | Gravener et al. |
| 4,473,077 A | 9/1984 | Noiles et al. |
| 4,476,863 A | 10/1984 | Kanshin et al. |

(Continued)

FOREIGN PATENT DOCUMENTS

| | | |
|---|---|---|
| EP | 0698376 A2 | 2/1996 |
| EP | 1790295 A1 | 5/2007 |

(Continued)

OTHER PUBLICATIONS

Japanese Office Action dated Dec. 20, 2018, issued in JP Appln. No. 2015055883.

(Continued)

*Primary Examiner* — Nathaniel C Chukwurah
(74) *Attorney, Agent, or Firm* — Carter, DeLuca & Farrell LLP

(57) ABSTRACT

A sled for use with an anvil assembly delivery system is provided which includes a body defining a concavity dimensioned to receive an anvil head of an anvil assembly and a recess dimensioned to receive a center rod of the anvil assembly. The body has a smooth outer profile to facilitate atraumatic trans-oral insertion of the anvil assembly to a surgical site. The body further defines a first suture channel on each side of the recess to facilitate securement of the body to the anvil assembly.

7 Claims, 20 Drawing Sheets

(56) References Cited

U.S. PATENT DOCUMENTS

| | | |
|---|---|---|
| 4,537,193 A | 8/1985 | Tanner |
| 4,573,468 A | 3/1986 | Conta et al. |
| 4,576,167 A | 3/1986 | Noiles |
| 4,603,693 A | 8/1986 | Conta et al. |
| 4,646,745 A | 3/1987 | Noiles |
| 4,667,673 A | 5/1987 | Li |
| 4,712,536 A | 12/1987 | Hawks |
| 4,773,417 A | 9/1988 | Moore et al. |
| 4,817,847 A | 4/1989 | Redtenbacher et al. |
| 4,873,977 A | 10/1989 | Avant et al. |
| 4,976,684 A | 12/1990 | Broadnax, Jr. |
| 5,005,749 A | 4/1991 | Aranyi |
| 5,047,039 A | 9/1991 | Avant et al. |
| 5,104,025 A | 4/1992 | Main et al. |
| 5,108,420 A | 4/1992 | Marks |
| 5,119,983 A | 6/1992 | Green et al. |
| 5,234,438 A | 8/1993 | Semrad |
| 5,275,622 A | 1/1994 | Lazarus et al. |
| 5,314,435 A | 5/1994 | Green et al. |
| 5,531,785 A | 7/1996 | Love et al. |
| 5,588,579 A | 12/1996 | Schnut et al. |
| 5,766,187 A | 6/1998 | Sugarbaker |
| 5,851,195 A | 12/1998 | Gill |
| 5,893,865 A | 4/1999 | Swindle et al. |
| 6,053,390 A | 4/2000 | Green et al. |
| 6,149,660 A | 11/2000 | Laufer et al. |
| 6,673,088 B1 | 1/2004 | Vargas et al. |
| 6,918,871 B2 | 7/2005 | Schulze |
| 7,004,175 B2 | 2/2006 | LaFontaine et al. |
| 7,144,405 B2 | 12/2006 | Vargas et al. |
| 7,168,604 B2 | 1/2007 | Milliman et al. |
| 7,179,267 B2 | 2/2007 | Nolan et al. |
| 7,628,795 B2 | 12/2009 | Karwoski et al. |
| 9,655,626 B2 * | 5/2017 | Williams ........... A61B 17/1155 |
| 2003/0181938 A1 | 9/2003 | Roth et al. |
| 2004/0087977 A1 | 5/2004 | Nolan et al. |
| 2005/0277962 A1 | 12/2005 | Myers |
| 2006/0229643 A1 | 10/2006 | Nolan et al. |
| 2007/0088389 A1 | 4/2007 | Dunkin et al. |
| 2007/0106217 A1 | 5/2007 | DeLegge et al. |
| 2008/0172087 A1 | 7/2008 | Fuchs et al. |
| 2009/0250502 A1 | 10/2009 | Milliman |
| 2009/0299377 A1 | 12/2009 | Bright |

FOREIGN PATENT DOCUMENTS

| | | |
|---|---|---|
| EP | 2039316 A2 | 3/2009 |
| EP | 2153781 A2 | 2/2010 |
| JP | 2009072599 A | 4/2009 |
| JP | 2010042259 A | 2/2010 |
| WO | 8706448 A1 | 11/1987 |
| WO | 0166020 A2 | 9/2001 |
| WO | 0200121 | 1/2002 |
| WO | 03030745 A1 | 4/2003 |

OTHER PUBLICATIONS

Australian Office Action dated Feb. 6, 2019, issued in AU Appln. No. 2015200756.

European Search Report dated Sep. 18, 2015, issued in EP Application No. 15165170.

* cited by examiner

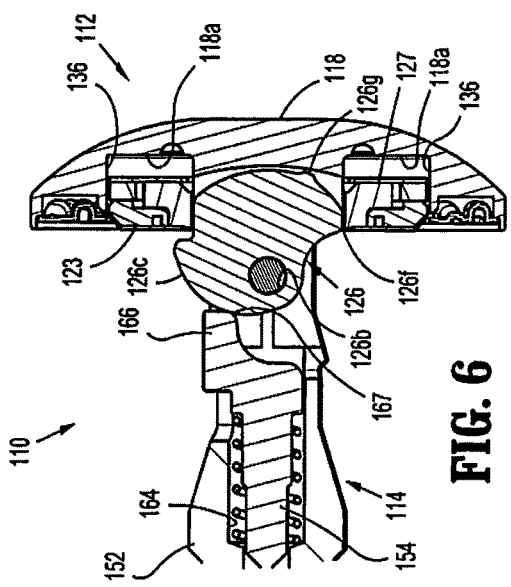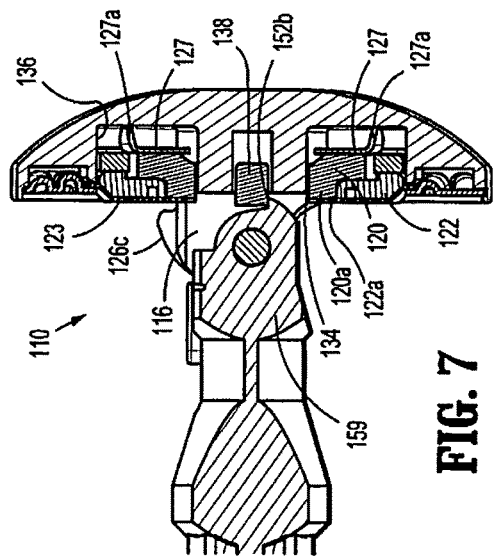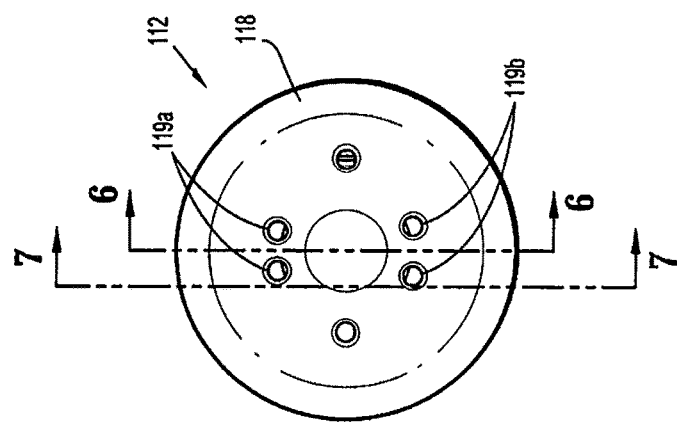

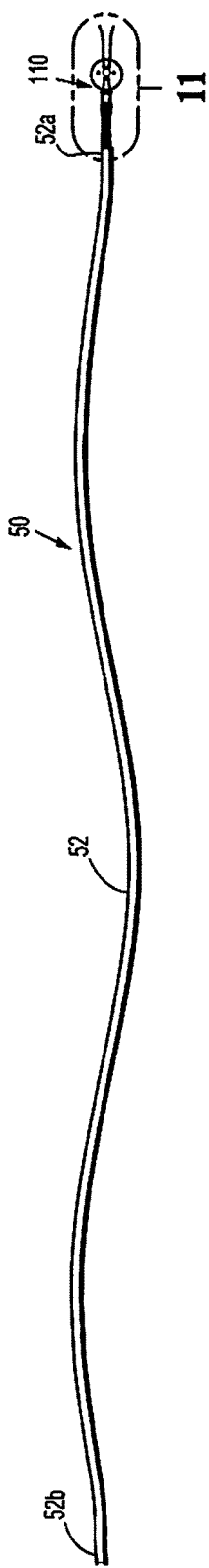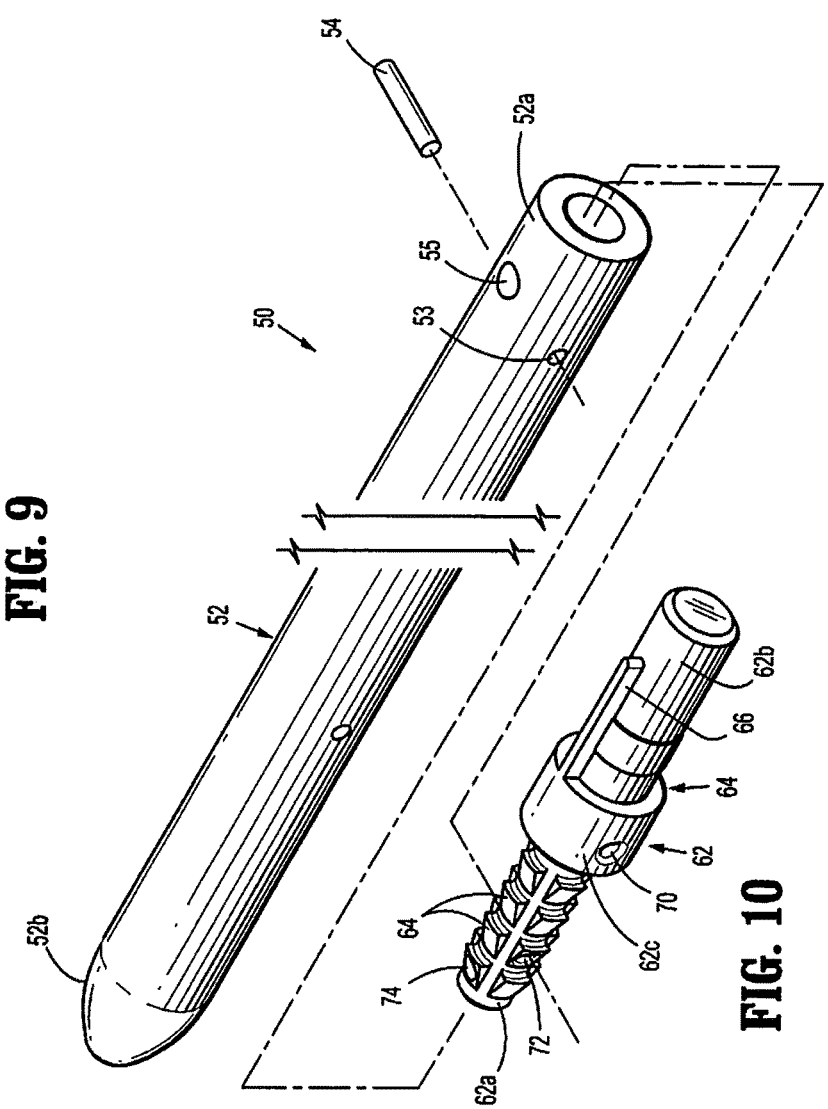
FIG. 9
FIG. 10

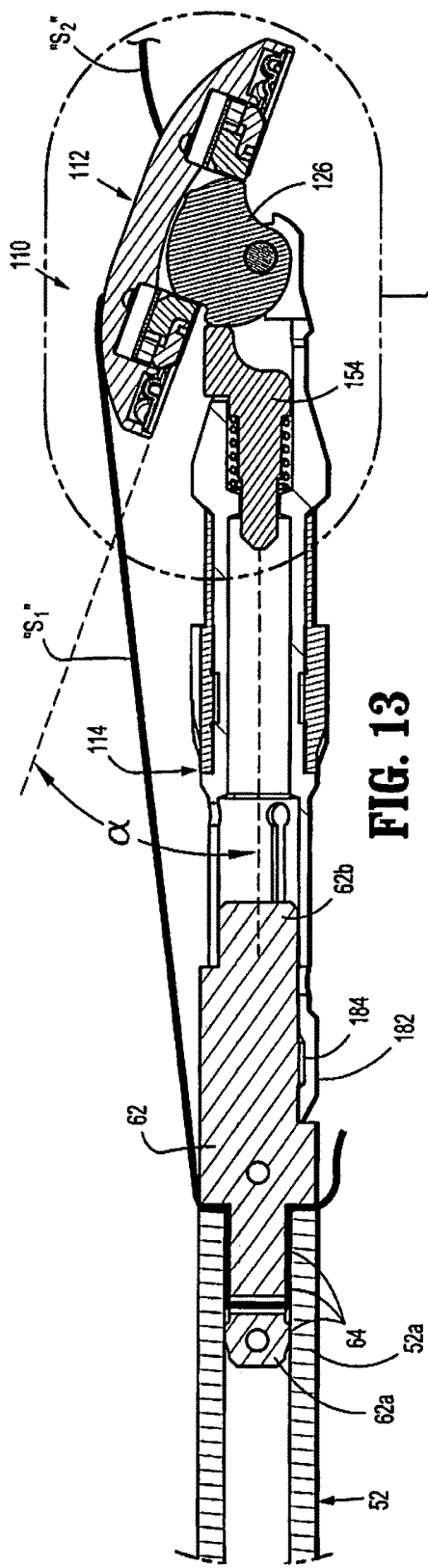
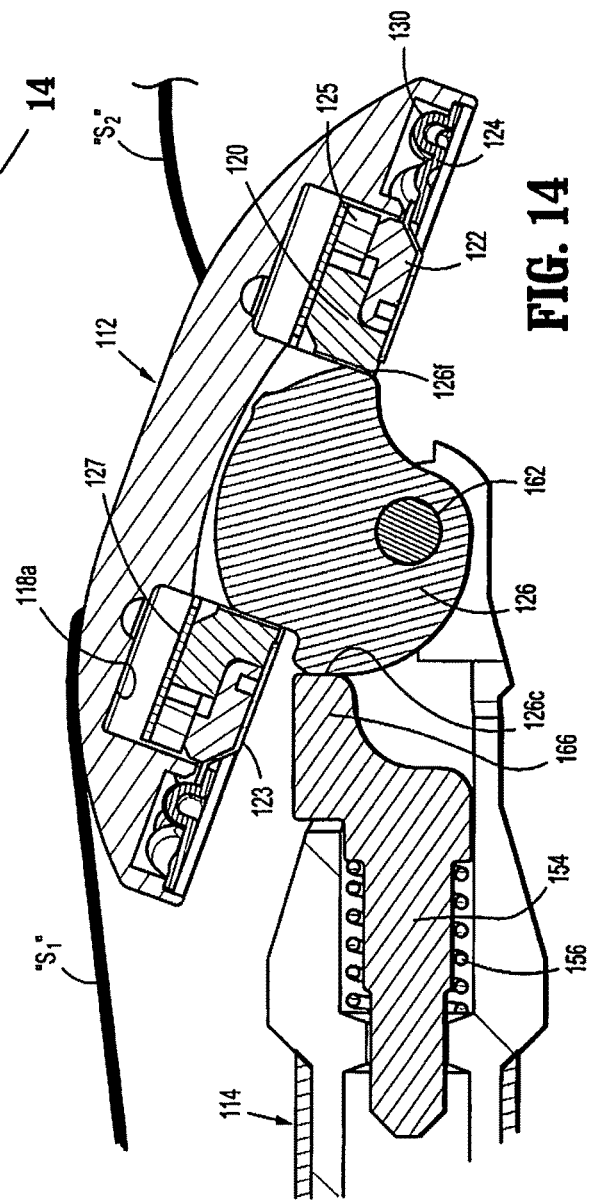
FIG. 13
FIG. 14

ANVIL ASSEMBLY DELIVERY SYSTEM

CROSS-REFERENCE TO RELATED APPLICATIONS

The present application is a Continuation Application which claims the benefit of and priority to U.S. patent application Ser. No. 14/263,412, filed on Apr. 28, 2014, now U.S. Pat. No. 9,655,626, the entire content of which is incorporated herein by reference.

TECHNICAL FIELD

The present disclosure relates generally to an anvil assembly delivery system for delivering an anvil assembly of a surgical stapling device to a surgical site. More specifically, the present disclosure relates to an anvil assembly delivery system including a sled for guiding an anvil assembly of a surgical stapling device trans-orally to a surgical site.

BACKGROUND

Anvil assembly delivery systems for trans-orally delivering an anvil assembly of a surgical stapling device to a surgical site are known. In known delivery systems, the anvil assembly is maintained in a tilted position to reduce the profile of a head of the anvil assembly to facilitate trans-oral delivery. Additional improvements which facilitate atraumatic trans-oral delivery of an anvil assembly to a surgical site would be desireable.

SUMMARY

A sled for use with an anvil assembly delivery system is provided which includes a body defining a concavity dimensioned to receive an anvil head of an anvil assembly and a recess dimensioned to receive a center rod of the anvil assembly. The body has a smooth outer profile to facilitate atraumatic trans-oral insertion of the anvil assembly to a surgical site. The body further defines a first suture channel on each side of the recess to facilitate securement of the body to the anvil assembly.

In embodiments, the body includes a pair of spaced arms which define the recess. The first suture channels can be formed on or through the spaced arms.

In certain embodiments, the body includes a retaining portion which extends at least partially over the concavity.

In embodiments, the arms extend from a first end of the body and the retaining portion extends from a second end of the body towards the first end of the body.

In certain embodiments, the retaining portion defines a second suture channel.

In embodiments, the first end of the body defines a through bore which is dimensioned to receive a retrieval suture.

In certain embodiments, the first suture channels and the second suture channel are formed in raised eyelets.

In embodiments, the first suture channels include a pair of proximal suture channels and a pair of distal suture channels.

In certain embodiments, the proximal suture channels are spaced from the distal suture channels, and one of the proximal suture channels and one of the distal suture channels are positioned on each side of the recess in the body.

An anvil delivery system is also provided which includes a sled having a body defining a concavity and a recess, a flexible tube having a first closed end and a second end, an anvil assembly including a center rod and an anvil head assembly, and a first suture positioned through the suture channels to secure the anvil head assembly within the concavity of the body of the sled. The anvil assembly is secured to the second end of the flexible tube and the center rod of the anvil assembly is supported within the recess of the body.

In certain embodiments, the body of the sled includes a retaining portion which extends at least partially over the concavity to retain the anvil head assembly within the concavity.

In embodiments, the retaining portion of the body defines a second suture channel which receives the first suture to facilitate securement of the anvil head assembly within the concavity of the body of the sled.

In certain embodiments, the sled defines a through bore anvil, the anvil delivery system further includes a retrieval suture extending through the through bore to facilitate manipulation and retrieval of the anvil assembly.

In embodiments, the anvil head assembly is pivotally secured to the anvil center rod and is pivotal from a first tilted position to a non-tilted operative position.

In certain embodiments, the anvil delivery system includes an adapter connecting the flexible tube to the center rod of the anvil assembly.

In embodiments, the first suture is secured to the adapter to retain the anvil head assembly in the first tilted position.

BRIEF DESCRIPTION OF THE DRAWINGS

Various embodiments of the presently disclosed anvil assembly and anvil assembly delivery system are disclosed herein with reference to the drawings wherein:

FIG. 5 is an end view of the anvil assembly of FIGS. 1-4;

FIG. 6 is a cross-sectional side view of a distal end of the tilt anvil assembly of FIGS. 1-6 taken along line 6-6 of FIG. 5;

FIG. 7 is a cross-sectional side view of a distal end of the anvil assembly of FIGS. 1-6 taken along line 7-7 of FIG. 5;

FIG. 9 is a top view of the anvil assembly of FIGS. 1-7 supported on an anvil delivery system;

FIG. 10 is an enlarged exploded view of the anvil delivery system of FIG. 9;

FIG. 13 is a cross sectional side view of the anvil assembly of FIGS. 1-7, in a pre-fired tilted position supported on the anvil delivery system of FIGS. 9-12;

FIG. 14 is an enlarged view of the indicated area of detail shown in FIG. 13;

DETAILED DESCRIPTION OF EMBODIMENTS

Figure 1:
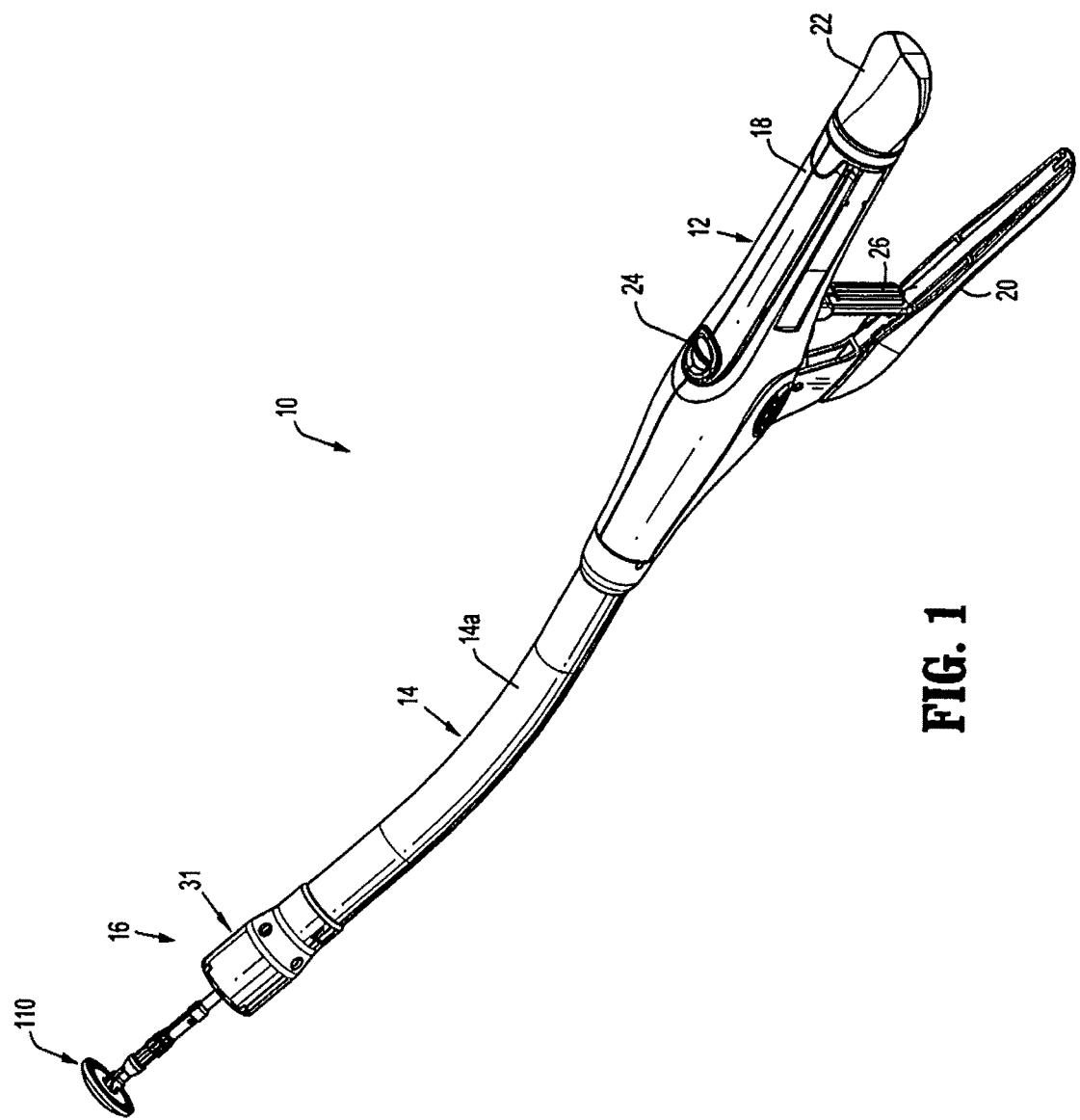
FIG. 1 is a perspective view of a surgical stapling device including an embodiment of an anvil assembly according to the present disclosure.
Figure 2:
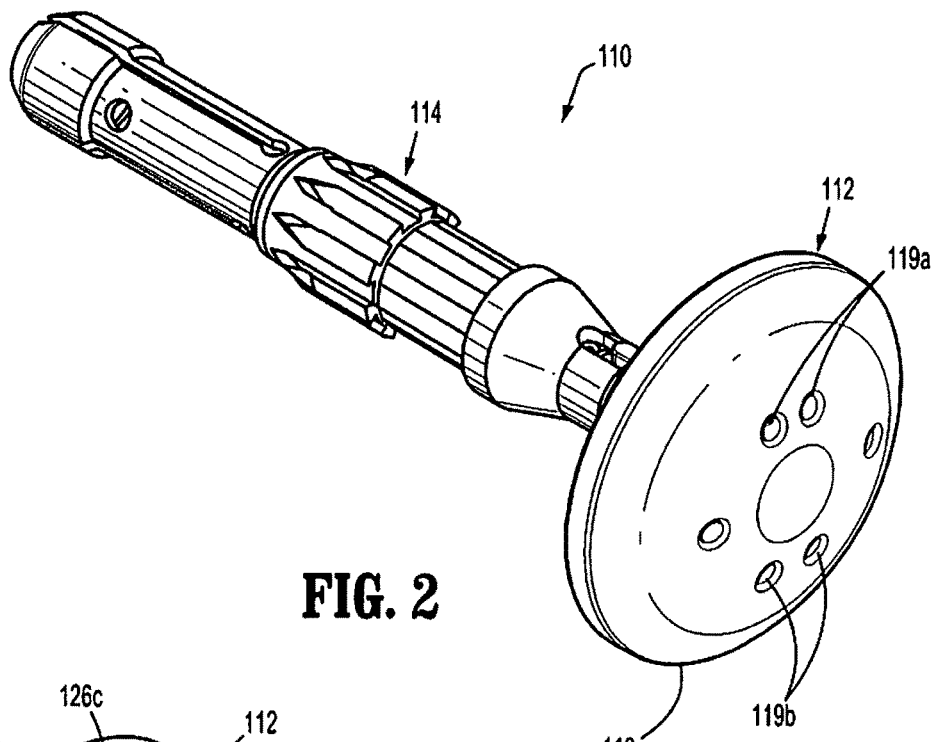
FIG. 2 is a first perspective side view of the anvil assembly of FIG. 1.

Embodiments of the presently disclosed anvil assembly delivery system will now be described in detail with reference to the drawings in which like reference numerals designate identical or corresponding elements in each of the several views. Throughout this description, the term "proximal" will refer to the portion of the instrument closest to the operator and the term "distal" will refer to the portion of the instrument furthest from the operator.

FIG. 1 illustrates an embodiment of a surgical stapling device configured for use with a tilt anvil assembly according to the present disclosure. Briefly, surgical stapling device 10 includes a proximal handle assembly 12, an elongated central body portion 14 including a curved elongated outer tube 14a, and a distal head portion 16. Alternately, in some surgical procedures, e.g., the treatment of hemorrhoids, it is desirable to have a substantially straight, shortened, central body portion. The length, shape and/or the diameter of body portion 14 and distal head portion 16 may also be varied to suit a particular surgical procedure.

With reference still to FIG. 1, handle assembly 12 includes a stationary handle 18, a firing trigger 20, a rotatable approximation knob 22 and an indicator 24. A pivotally mounted trigger lock 26 is fastened to handle assembly 12 and is manually positioned to prevent inadvertent firing of stapling device 10. Indicator 24 is positioned on the stationary handle 18 and includes indicia, e.g., color coding, alpha-numeric labeling, etc., to identify to a surgeon whether the device is approximated and is ready to be fired. Head portion 16 includes an anvil assembly 110 and a shell assembly 31. For a more detailed discussion of surgical stapler 10, please refer to commonly owned U.S. Pat. No. 7,364,060 to Milliman, the contents of which is incorporated herein by reference in its entirety.

Referring now to FIGS. 2-7, an embodiment of the present disclosure is shown generally as anvil assembly 110. Anvil assembly 110 is shown in a non-titled position or operative position. Anvil assembly 110 includes a head assembly 112 and a center rod assembly 114. Head assembly 112 includes a post 116, a housing 118, a backup member or plate 120, a cutting ring 122, a cutting ring cover 123, an anvil plate 124, a spacer or washer 125, a cam latch member 126, and a retainer member 127. Post 116 is monolithically formed with and centrally positioned within housing 118. Alternately, housing 118 and post 116 may be formed separately and fastened together using a known fastening technique, e.g., welding.

As will be discussed in further detail below, housing 118 includes openings 119a, 119b sized and dimensioned to receive one or more sutures "S". During use, a first suture "$S_1$" (FIG. 9) is inserted through openings 119a and is used to retain head assembly 112 in a retracted or first tilted position (FIG. 9) during insertion of anvil assembly 110 within a patient. A second suture "$S_2$" (FIG. 9) is inserted through openings 119b and is configured to permit retrieval of tilt anvil assembly 110 from within a patient. During trans-oral insertion of anvil assembly 110, suture "$S_2$" extends from the mouth of patient, permitting the anvil assembly 110 to be retrieved trans-orally.

With reference still to FIGS. 2-7, anvil plate 124 is supported in an outer annular recess 128 of housing 118 and includes a plurality of staple deforming pockets 130 for receiving and deforming staples. At least one tab 124a extends radially outwardly from anvil plate 124 and is received within a cutout 132 formed in an outer rim of housing 118. Tab 124a and cutout 132 function to align or properly position anvil plate 124 within annular recess 128 of housing 118.

With particular reference to FIGS. 6 and 7, head assembly 112 will be described in detail. Backup plate 120 includes a central opening 134 which is positioned about post 116 within an inner annular recess 136 of housing 118 between post 116 and outer annular recess 128. Backup plate 120 includes a raised platform 120a. Cutting ring 122 includes an opening 122a having a configuration substantially the same as platform 120a. Although platform 120a is illustrated as having a circular shape, other configurations are envisioned, e.g., square, rectangular, triangular, etc. In one embodiment, cutting ring 122 is formed from polyethylene and is fixedly secured to backup plate 120 using, for example, an adhesive, to form a backup plate/cutting ring assembly. Backup plate 120 is formed from a hard material, e.g., a metal. Alternately other materials of construction may be used to construct backup plate 120 and cutting ring 122. Further, backup plate 120 and cutting ring 122, in the alternative, can be formed as a single or unitary structure.

Still referring to FIGS. 6 and 7, a cutting ring cover 123 is secured to an outwardly facing or proximal surface of cutting ring 122 using, for example, an adhesive. In one embodiment, cutting ring cover 123 is formed from a material or materials, which have a hardness greater than that of the cutting ring, e.g., mylar. In one embodiment, cutting ring cover 123 includes two layers of mylar (not shown) which are joined together using an adhesive and a polypropylene coating. Alternately, cutting ring 122 need not have a cover. Cutting ring 122 and backup plate 120 are slidably mounted about post 116. Backup plate 120 includes a pair of inwardly extending fingers 138 which will be described in further detail below.

With reference still to FIGS. 6 and 7, retainer member 127 is positioned in inner annular recess 136 between backup plate 120 and a back wall 118a of housing 118. In one embodiment, retainer member 127 is annular and includes a plurality of deformable tabs 127a which engage a rear surface of backup plate 120. Retainer member 127 prevents backup plate 120 and cutting ring 122 from moving or being pushed into inner annular recess 136 of housing 118 until a predetermined force sufficient to deform tabs 127a has been applied to the backup plate/cutting ring assembly. The predetermined force can be close to but is less than the force applied by an annular cutting blade of a surgical stapling device when it engages, for example, the cutting ring of anvil assembly 110. In one embodiment by way of example, the predetermined force is between about ten pounds and about ninety pounds and can be about thirty (30) pounds. When the predetermined force is reached, e.g., during cutting of tissue, backup plate 120 is urged into inner annular recess 136 and compresses retainer member 127. It is envisioned that other crushable, deformable, collapsible or movement restricting members may be used to retain the backup plate/cutting ring assembly in a fixed position until a predetermined force has been applied to the backup plate/cutting ring assembly.

Turning back to FIG. 4, anvil center rod assembly 114 includes a center rod 152, a plunger 154 and plunger spring 156. A first end of center rod 152 includes a pair of arms 159 which define a cavity 159a. Each arm 159 has a transverse throughbore 158 which is aligned with a central longitudinal axis of center rod 152. Alternately, throughbores 158 can be offset from the longitudinal axis of center rod 152. Post 116 of anvil head assembly 112 is dimensioned to be positioned within cavity 159a and also includes a transverse throughbore (not shown). A pivot member 162 pivotally secures post 116 to center rod 152 via the through bores such that anvil head assembly 112 may be pivotally mounted to anvil center rod assembly 114.

Figure 3:
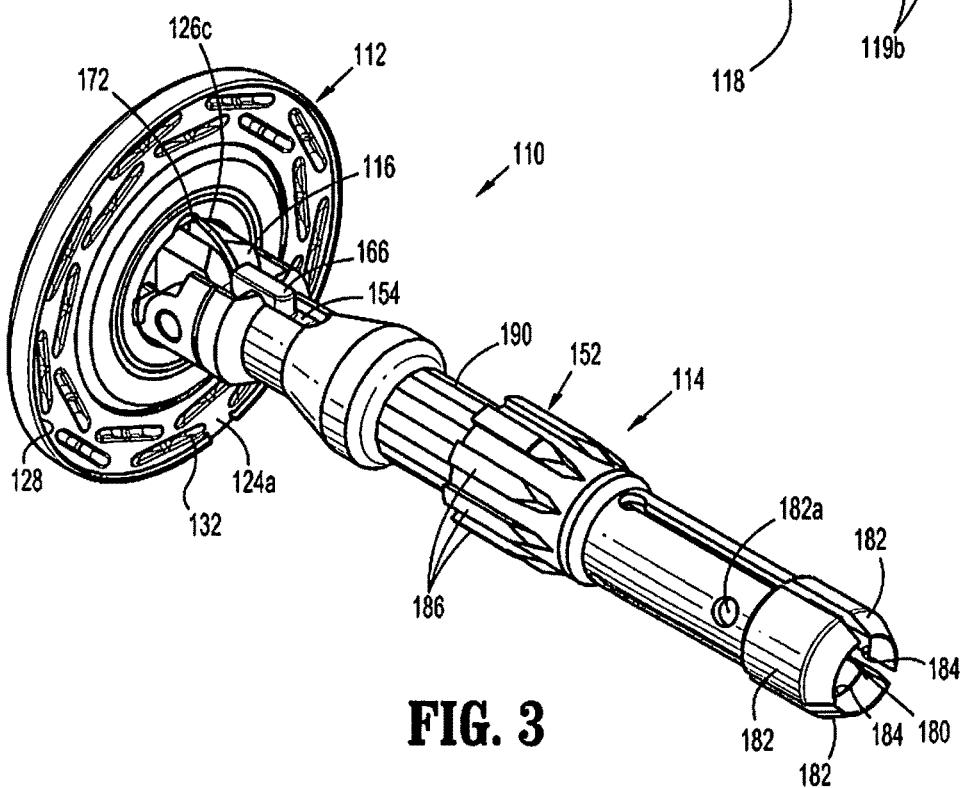
FIG. 3 is a second perspective side view of the anvil assembly shown in FIGS. 1 and 2.
Figure 8:
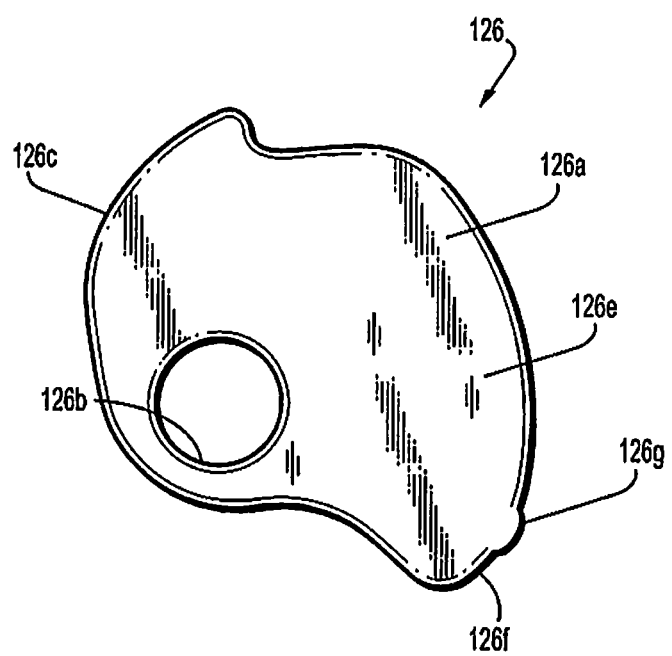
FIG. 8 is an enlarged side view of the cam latch member of the anvil assembly of FIGS. 1-7.
Figure 11:
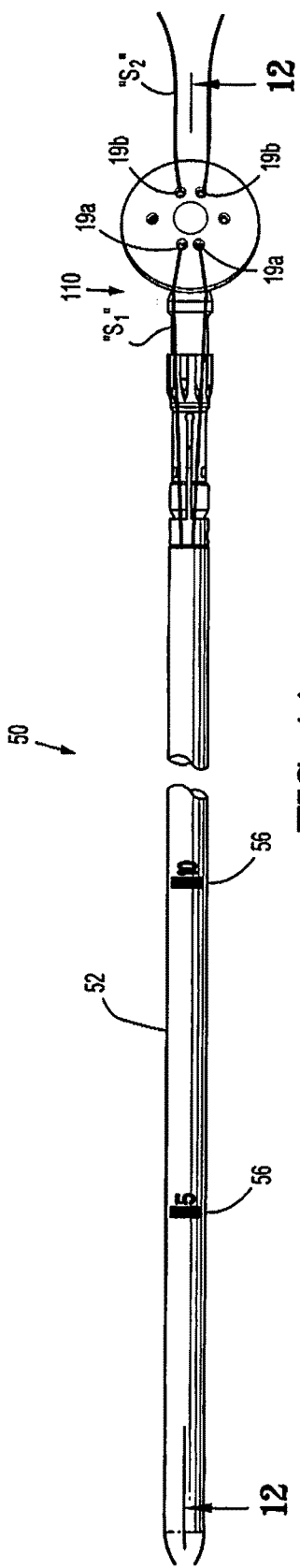
FIG. 11 an enlarged top view of the anvil delivery system of FIGS. 9 and 10, including the anvil assembly of FIGS. 1-7.
Figure 12:
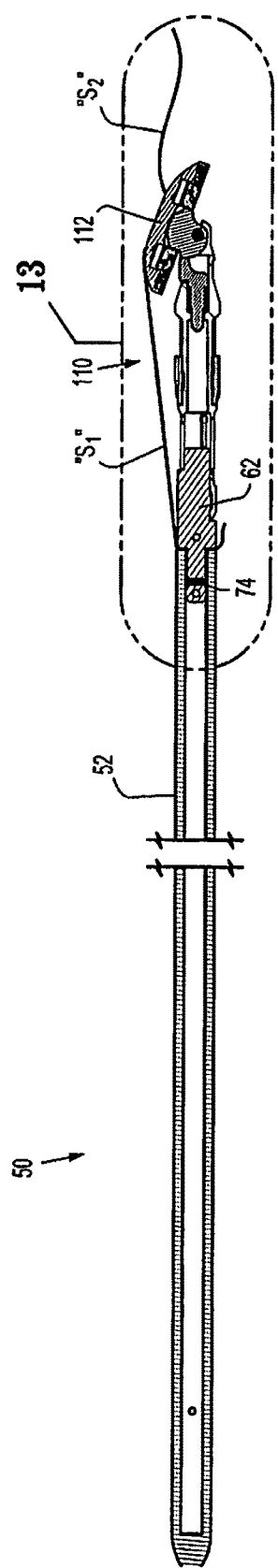
FIG. 12 is a cross-sectional side view of the anvil assembly and anvil assembly delivery system of FIG. 11 taken along lines 12-12 of FIG. 11.

Turning briefly to FIG. 8, cam latch member 126 includes a body 126a having a throughbore 126b. Throughbore 126b is dimensioned to receive pivot member 162 such that cam latch member 126 is pivotally mounted within transverse slot 172 (FIG. 3) of post 116 about pivot member 162. Referring now to FIGS. 3, 6 and 7, cam latch member 126 includes a first body portion 126c which extends partially from slot 172 of post 116 and is positioned to be engaged by a finger 166 of plunger 154. First body portion 126c is configured such that the distance between the surface of first body portion 126c and through bore 126b increase in a clockwise direction about cam latch member 126. In this manner, plunger 154 is able to move forward as cam latch member 126 rotates in a clockwise direction. Additionally, this configuration of first body portion 126c permits plunger 154 to be retracted as cam latch member rotates in a counter-clockwise direction. Cam latch member 126 also includes an edge 126f, including a tab 126b. A leading portion of edge 126f is configured to be urged into engagement with an inner periphery 120b of backup plate 120 by an engagement finger 166 of plunger 154 when anvil head 112 is in its non-tilted or operative position. Tab 126g is configured to engage backwall 118a of housing 118 to prevent cam latch member 126 from rotating counter-clockwise relative to housing 118.

With reference to FIG. 6, plunger 154 is slidably positioned in a bore 164 formed in the first end of center rod 152. Plunger 154 includes an engagement finger 166 which is offset from the pivot axis of anvil head assembly 112 and biased into engagement with an edge 126c of cam latch 126. Engagement of finger 166 with edge 126c of cam latch 126 presses a leading portion of edge 126f against an inner periphery of back plate 120 to urge anvil head assembly 112 to an operative or non-tilted position on center rod 152.

Turning to FIG. 7, in the pre-fired operative position of head assembly 112, i.e. when head assembly 112 has been pivoted to its non-tilted position, fingers 138 formed on backup plate 120 engage protrusions 152b adjacent top surface 152a of center rod 152 to prevent head assembly 112 from pivoting about pivot member 162. Anvil head assembly 112 may be tilted α degrees (FIG. 13) relative to anvil center rod assembly 114 in the pre-fired tilted position. In one embodiment, anvil head assembly 112 is tilted about seventy degrees (70°) in its pre-fired tilted position; however it should be understood that tilting head assembly 112 to other degrees is also contemplated. Titling of anvil head assembly 112 relative to anvil center rod assembly 114 causes body portion 126c of cam latch member 126 to engage finger 166 of plunger 154. As cam latch assembly 126 rotates with the tilting of anvil head assembly 112, plunger 154 is retracted with bore 164 of anvil center rod assembly 114, thereby compressing spring 156. In this manner, finger 166 of plunger 154 is distally biased against body portion 126c of cam latch member 126.

Figure 4:
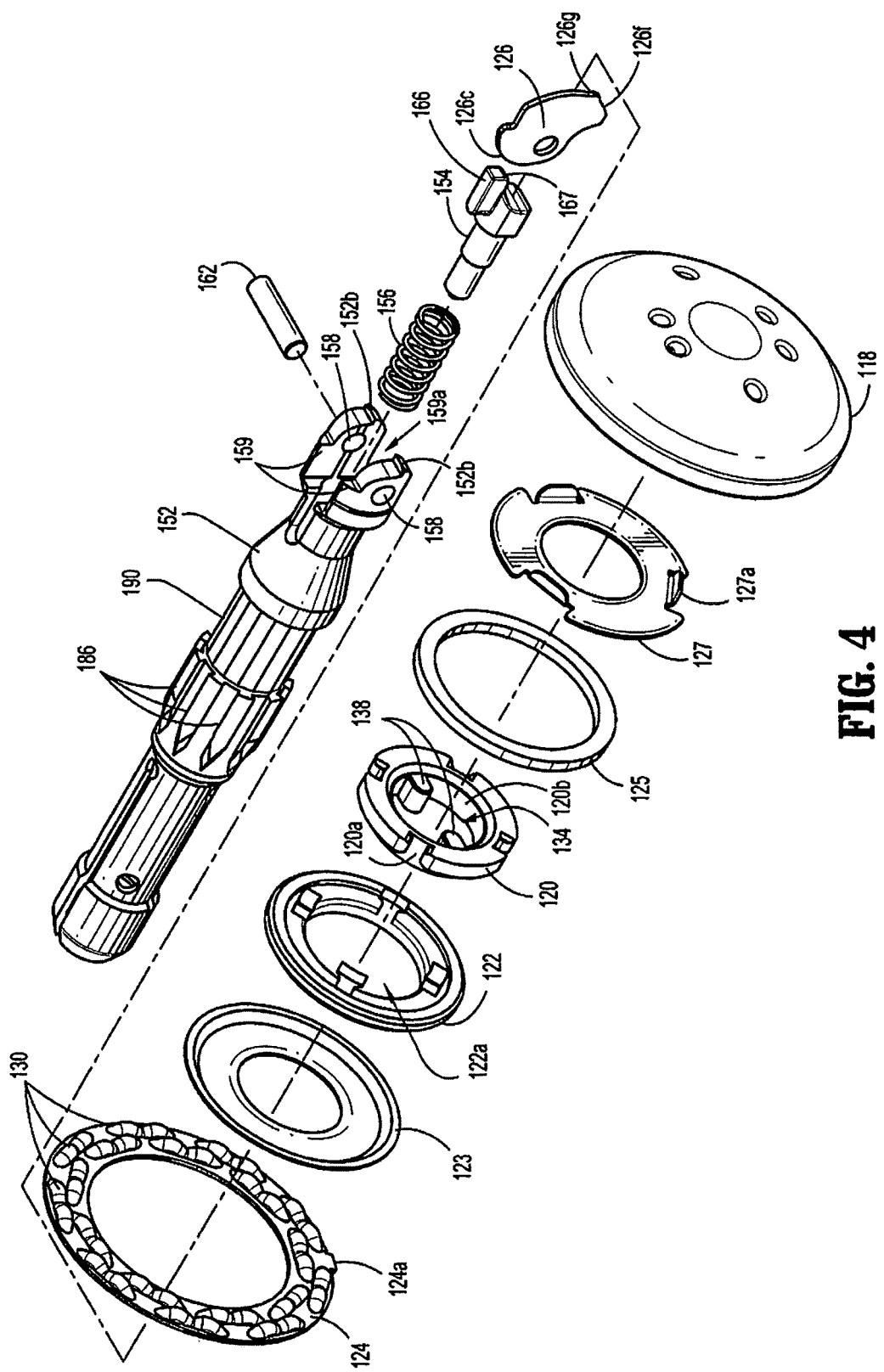
FIG. 4 is an exploded side view of the anvil assembly of FIGS. 1-3.
Figure 18:
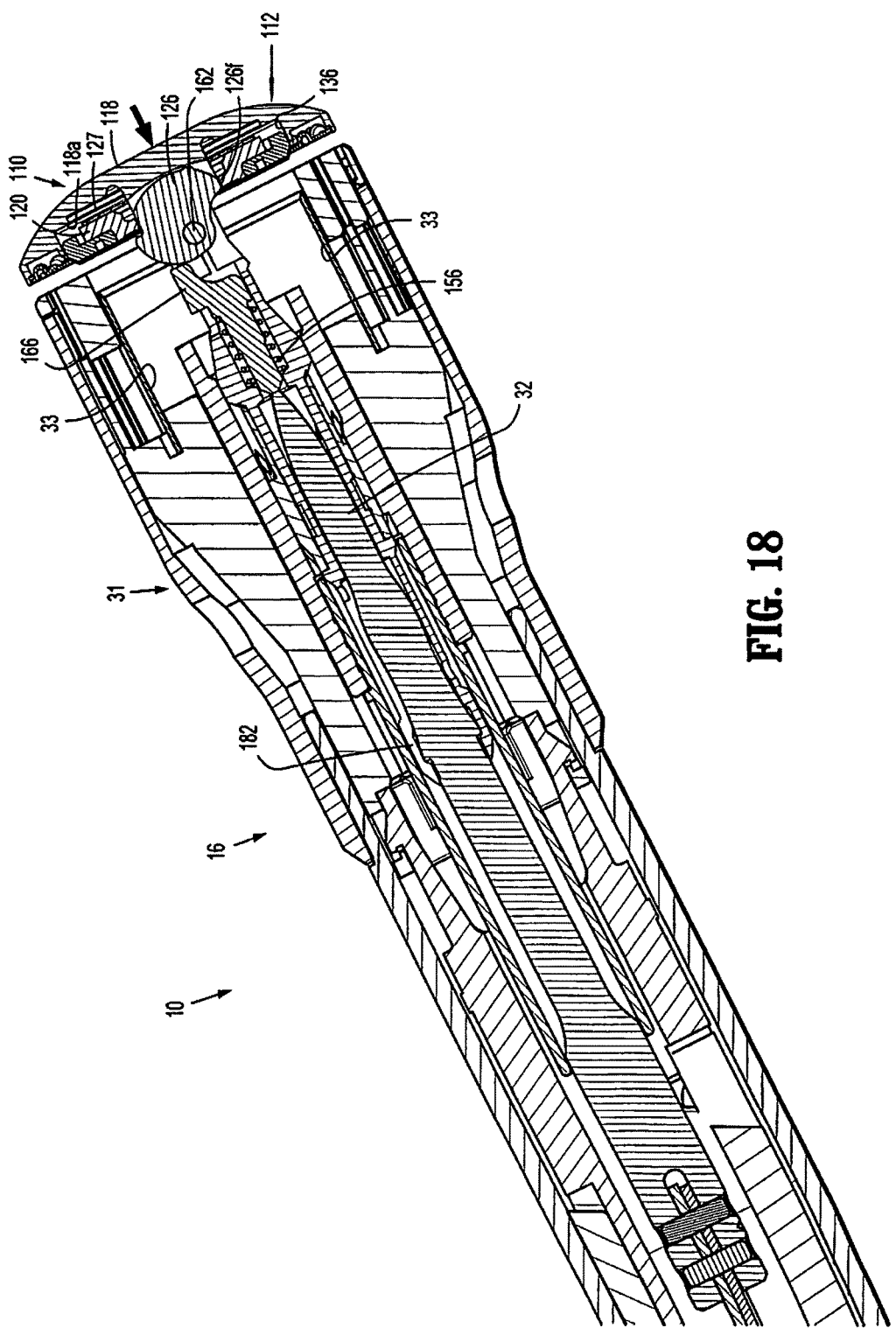
FIG. 18 is an enlarged cross-sectional side view of the distal head portion of the surgical stapling device of FIG. 1 and the anvil assembly of FIGS. 1-7 in a pre-fired non-tilted operative position.
Figure 19:
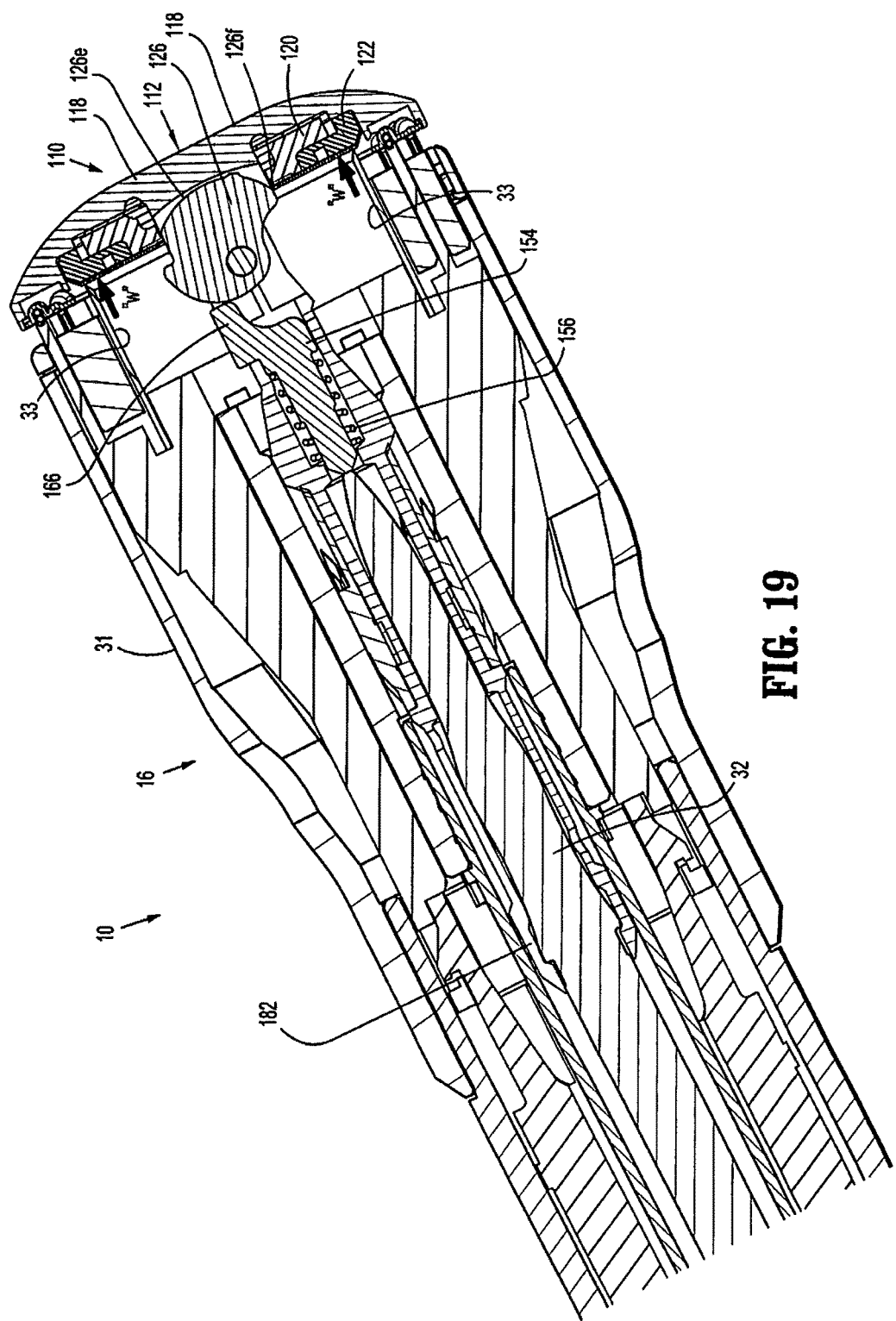
FIG. 19 is an enlarged cross-sectional side view of the distal head portion of the surgical stapling device of FIG. 1 and the anvil assembly of FIGS. 1-7 in a post-fired non-titled operative position.
Figure 20:
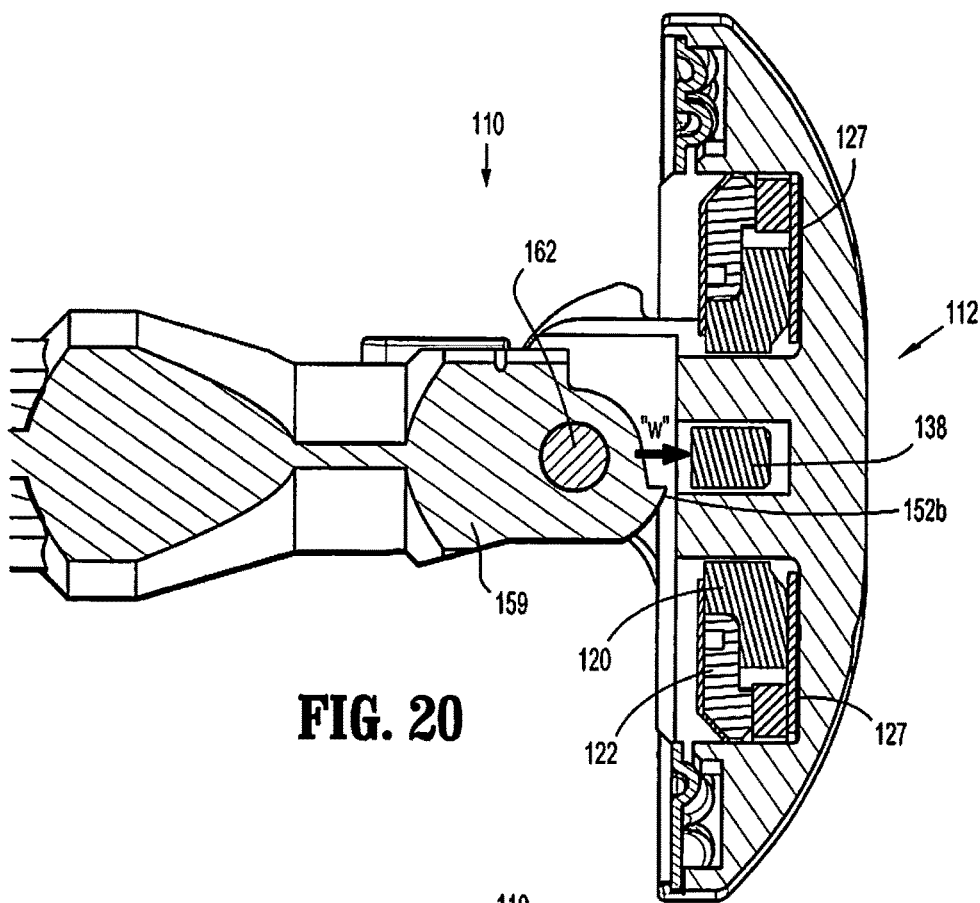
FIG. 20 is an enlarged cross-sectional side view of the distal end of the anvil assembly of FIGS. 1-7 in the post-fired operative position.
Figure 21:
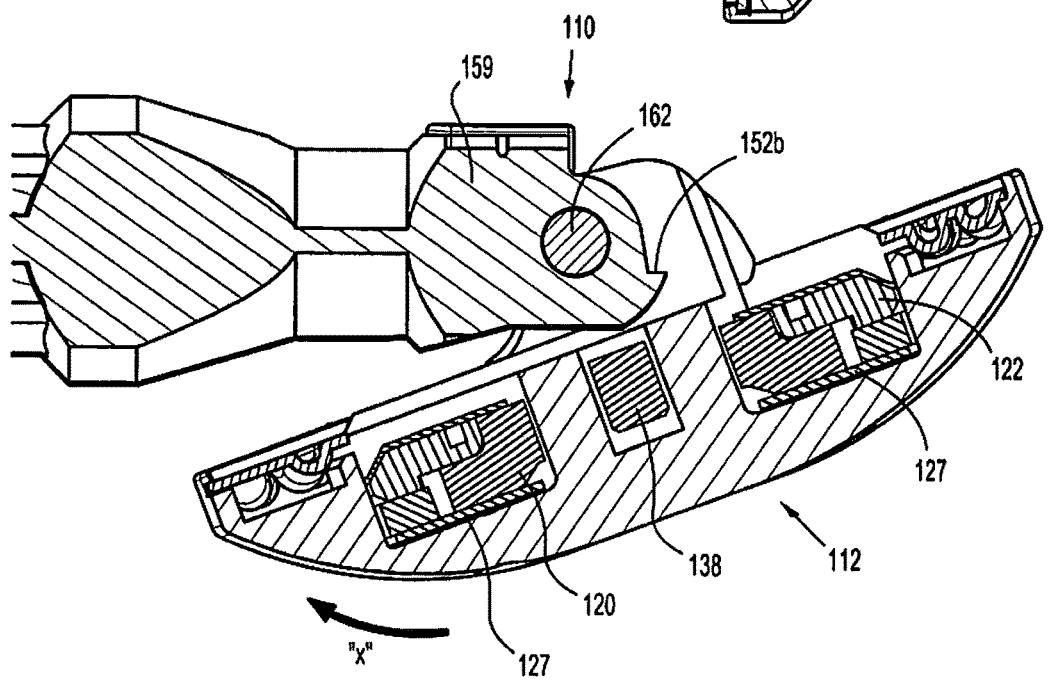
FIG. 21 is an enlarged cross-sectional side view of the distal end of the anvil assembly of FIGS. 1-7 in a post-fired tilted position.

With reference to FIGS. 3 and 4, a second end of center rod 152 includes a bore 180 defined by a plurality of flexible arms 182. Flexible arms 182 each include an opening 182a dimensioned to receive a projection formed on or connected to a shell assembly 31 (FIG. 18). Alternatively, openings 182a may be configured to receive a suture for permitting retrieval of anvil assembly 110. The proximal ends of each of the flexible arms 182 include an internal shoulder 184 dimensioned to releasably engage shell assembly 31 of surgical stapling device 10 to secure anvil assembly 110 to the surgical stapling device. A plurality of splines 186 are formed about center rod 152. Splines 186 function to align anvil assembly 110 with the staple holding portion of a surgical stapling device. Center rod 152 also includes an annular recessed portion 190 to facilitate grasping of anvil assembly 110 by a surgeon with a grasper. Recessed portion 190 may include a roughened or knurled surface or an overmold to facilitate grasping of anvil assembly 110.

With reference now to FIGS. 9-12, a system for delivering anvil assembly 110 within a patient is shown generally as anvil delivery system 50. Anvil delivery system 50 includes a flexible tube 52 and an adapter 62. Flexible tube 52 includes an open end 52a. Adapter 62 and anvil assembly 110 are supported on open end 52a of flexible tube 52. Open end 52a of flexible tube 52 includes a through bore 53 extending therethrough configured to receive a locking pin 54. Open end 52a further includes an opening 55. Closed end 52b of flexible tube 52 is configured for trans-orally receipt in a patient. Flexible tube 52 may include markings or other gradations 56 along the length thereof to indicate to a surgeon how much of flexible tube 52 has been received within the patient during insertion and/or to indicate the length of flexible tube 52 remaining in the patient upon removal.

With particular reference to FIG. 10, adapter 62 includes a first end 62a configured to be received within open end 52a of flexible tube 52 and a second end 62b is configured to be received with in bore 180 formed in center rod 152 of anvil assembly 110. First end 62a includes a series of annular rings 64 configured to frictionally retain first end 62a of adapter 62 within open end 52a of flexible tube 52. Second end 62b of adapter 62 includes a longitudinal guide member 66 configured to be received between flexible arms 182 formed in center rod 152 of anvil assembly 110. In addition, second end 62b of adapter 62 is sized to allow center rod 154 of anvil assembly 110 to freely slide into and off second end 62b of adapter 62. Adapter 62 further includes a first through bore 70 formed in a central hub portion 62c as well as second and third through bores 72, 74 formed in first end 62a. Through bore 72 is configured to align with through bore 53 formed in open end 52a of flexible tube 52 and is sized to receive locking pin 54.

With particular reference now to FIGS. 10, 13 and 14, anvil assembly 110 is supported on anvil delivery system 50. Securing anvil assembly 110 to anvil delivery system 50 requires first that suture "$S_1$" is thread through openings 119a formed on anvil head 112 such that first and second ends of suture "$S_1$" are positioned on opposites of center rod 152. Next, second end 62b of adapter 62 is positioned within through bore 180 of center rod 152 such that longitudinal guide 66 is received between two of arm members 182. Each of the first and second ends of suture "$S_1$" is inserted through opening 55 formed in open end 52a of flexible member 52. Anvil head 112 is then rotated to a first tilted position while first and second ends of suture "$S_1$" are pulled through opening 55. First end 62a of adapter 62 is then inserted into open end 52a of flexible member. The frictional contact between annular rings 64 of first end 62a of adapter 62 and an inner surface of flexible tube 52 secures adapter 62 to flexible tube 52 and prevents suture "$S_1$" from loosening. It is envisioned that more than one suture may be used to secure anvil head assembly 112 in a pre-fired tilted position.

Figure 15:
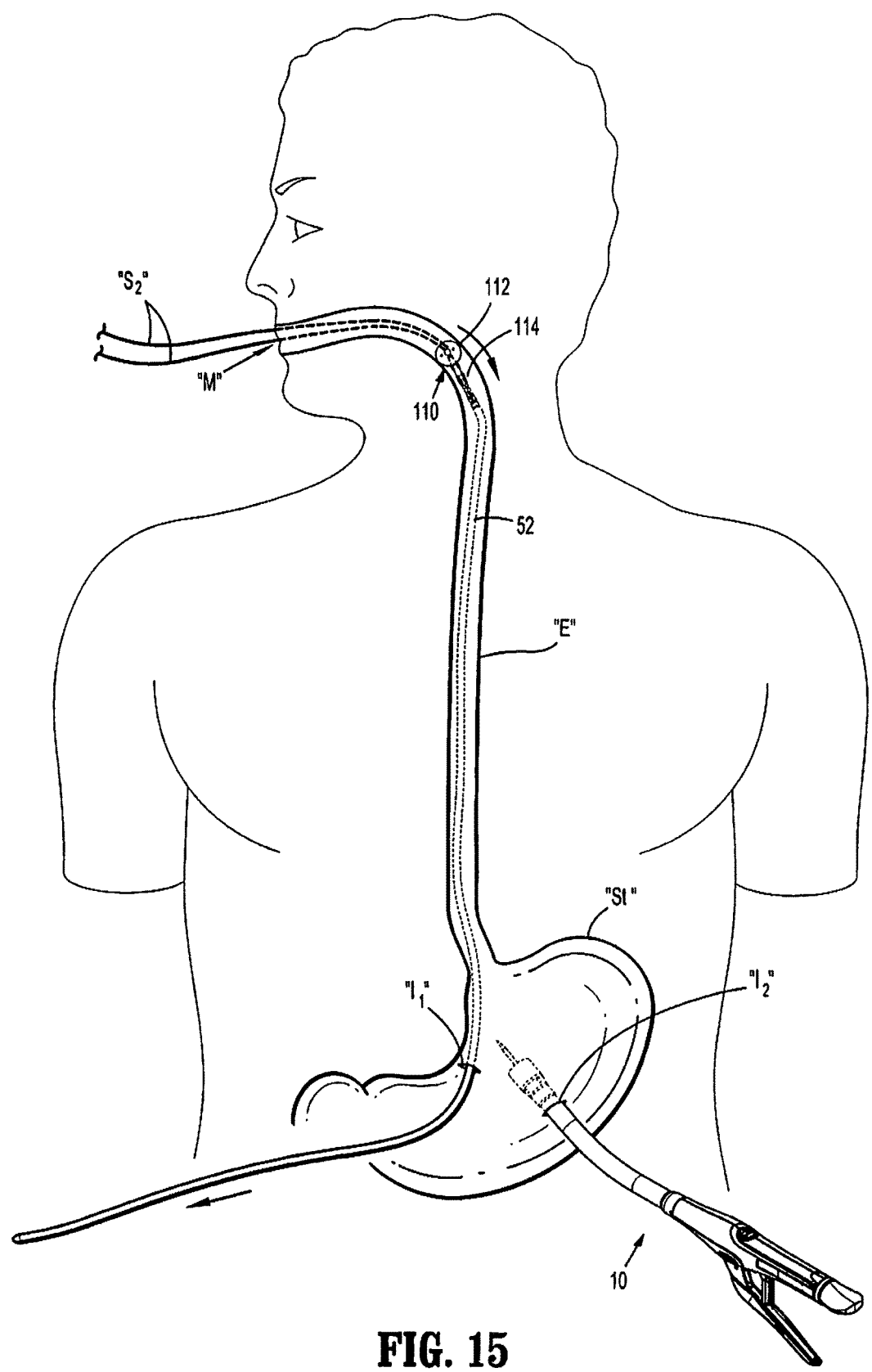
FIG. 15 is an illustration of the anvil assembly and anvil delivery system of FIGS. 11 and 12 being inserted trans-orally into a patient.

With reference now to FIG. 15, a method for delivering anvil assembly 110 to a surgical site within a patient will be described. In one method, anvil assembly 110 is provided in the first tilted position supported on anvil delivery system 50 and ready for delivery. Alternatively, a clinician secures anvil assembly 110 to anvil delivery system 50 as discussed above. Once anvil assembly 110 has been secured to flexible tube 52, the surgeon inserts closed end 52b of flexible tube 52 in the patient's mouth "M" and moves closed end 52b along with flexible tube 52 down through esophagus "E" to a surgical site, i.e., the stomach "St".

After insertion, the surgeon then makes a first incision "$I_1$" at the surgical site (stomach "St" as shown) to create an inner access to closed end 52b of flexible tube 52 and then pulls open end 52b of flexible tube 52 through first incision "$I_1$". In some procedures it may be beneficial to pull flexible tube 52 through incision "$I_1$" until center rod 152 of anvil assembly 110 advances through first incision "$I_1$". When anvil assembly 110 is properly positioned at the surgical site, the surgeon releases anvil delivery system 50 from anvil assembly 110 by cutting suture "$S_1$" and separating anvil assembly 110 from second end 62b of adapter 62. Flexible tube 52 (with fitting 62) may then be pulled from the body through first incision "$I_1$".

Severing of suture "$S_1$" permits plunger 154 to extend from within bore 164, thereby causing finger 166 to engage body portion 126c of cam latch member 126. Rotation of cam latch member 126 causes edge 126f of latch member 126 to move into engagement with the inner periphery of backup plate 120, thereby urging anvil head assembly 112 to return to a non-tilted operative position. Additionally, the distal end of stapling device 10 may be configured to engage finger 166 of plunger 154 as anvil assembly 110 is attached to surgical stapling device 10. In this manner, the distal end of surgical stapling device 10 urges plunger 154 distally, thereby ensuring the rotation of anvil head assembly 112 to a non-tilted position.

With particular reference to FIG. 15, in one method, a second incision "$I_2$" is then formed at the surgical site such that distal head portion 16 of surgical stapling device 10 may be received therethrough. Alternatively, distal head portion 16 of surgical stapling device 10 may be received through first incision "$I_1$" once anvil deliver system 50 has been removed therefrom.

Figure 16:
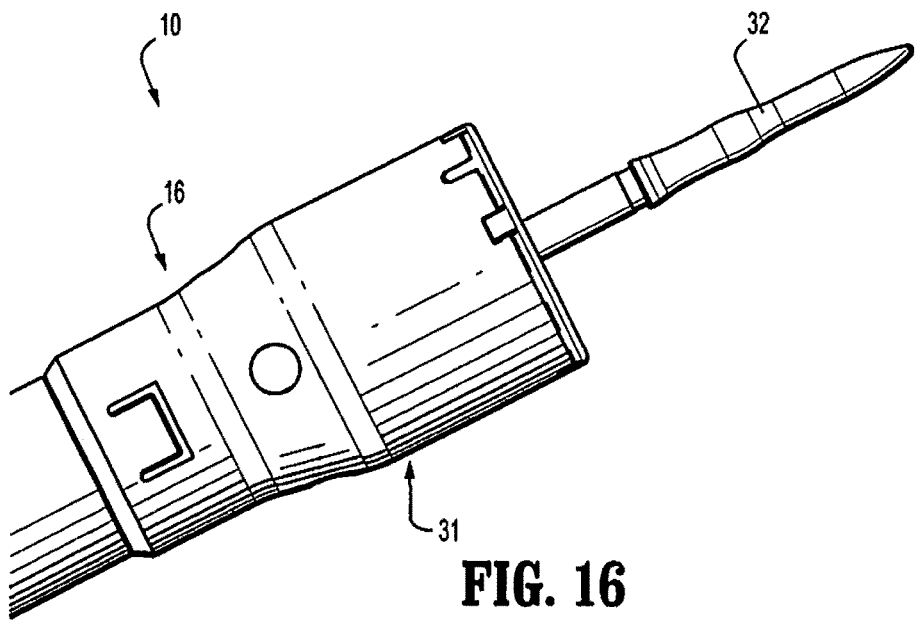
FIG. 16 is an enlarged side view of the distal head portion of the surgical stapling device of FIG. 1 with the anvil assembly removed.
Figure 17:
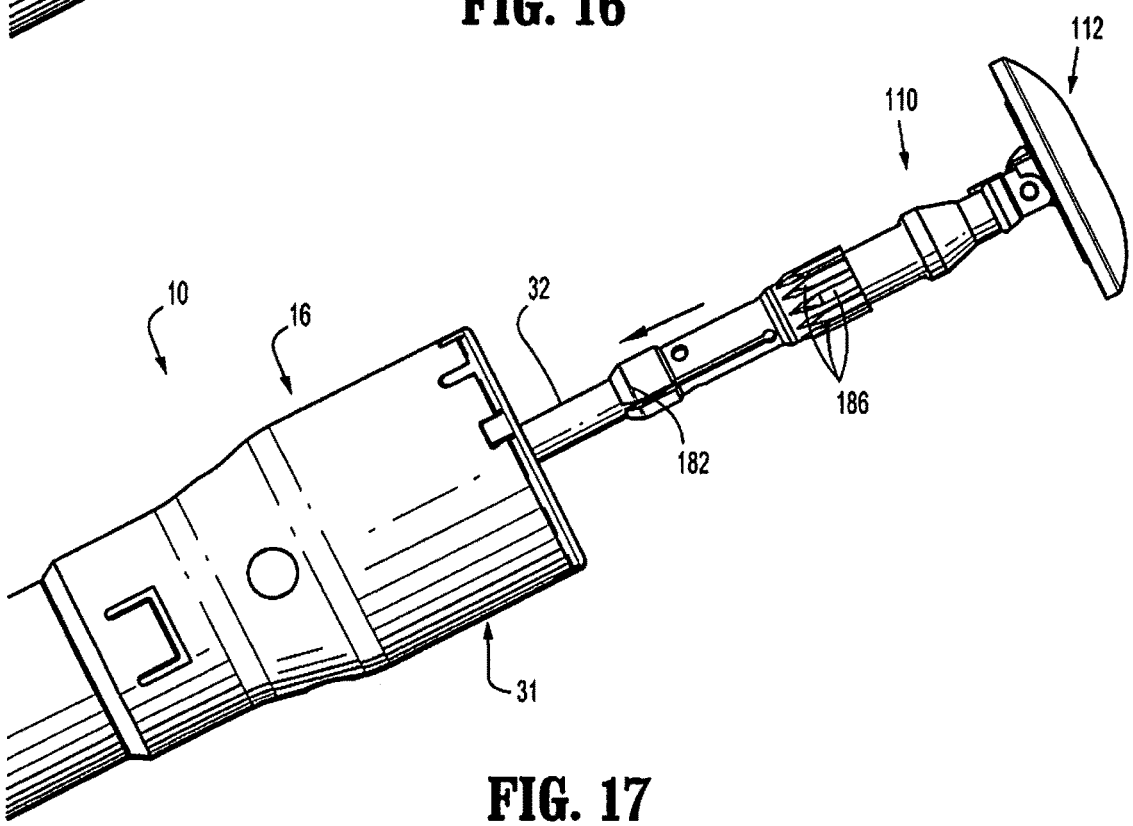
FIG. 17 is an enlarged side view of the distal head portion of the surgical stapling device of FIG. 1 with the anvil assembly of FIGS. 1-7 received thereon.

Turning briefly to FIGS. 16 and 17, anvil assembly 110 is operably received on an anvil retainer 32 extending from shell assembly 31 formed on a distal end of surgical stapling device 10. Once anvil assembly 110 is received on surgical stapling device 10, surgical stapling device 10 operates in the manner discussed in the '060 patent.

The operation of anvil assembly 110 will now be described with reference to FIGS. 18-23. When anvil assembly 110 is in its pre-fired non-tilted position, backup plate 120 is spaced from backwall 118a of housing 118 by retainer 127 and protrusions 152b of center rod 152 engage fingers 138 of backup plate 120 to prevent tilting of anvil head assembly 112 about pivot member 162. Finger 166 of plunger 154 is urged by spring 156 into engagement with body portion 126c of cam latch member 126 to urge cam latch member 126 in a clockwise direction, about pivot member 162 such that edge 126f of cam latch member 126 engages inner periphery 120b of backup member 120.

Figure 22:
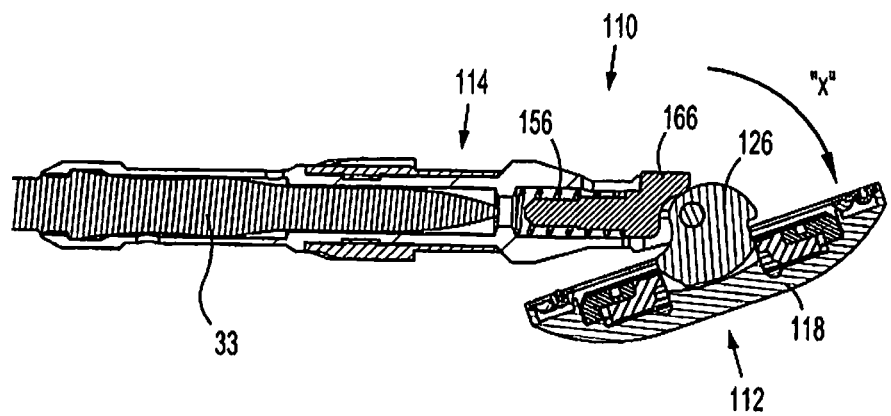
FIG. 22 is a cross-sectional side view of the anvil assembly of FIGS. 1-7 in a post-fired tilted position supported on an anvil retainer of the surgical instrument of FIG. 1.
Figure 22A:
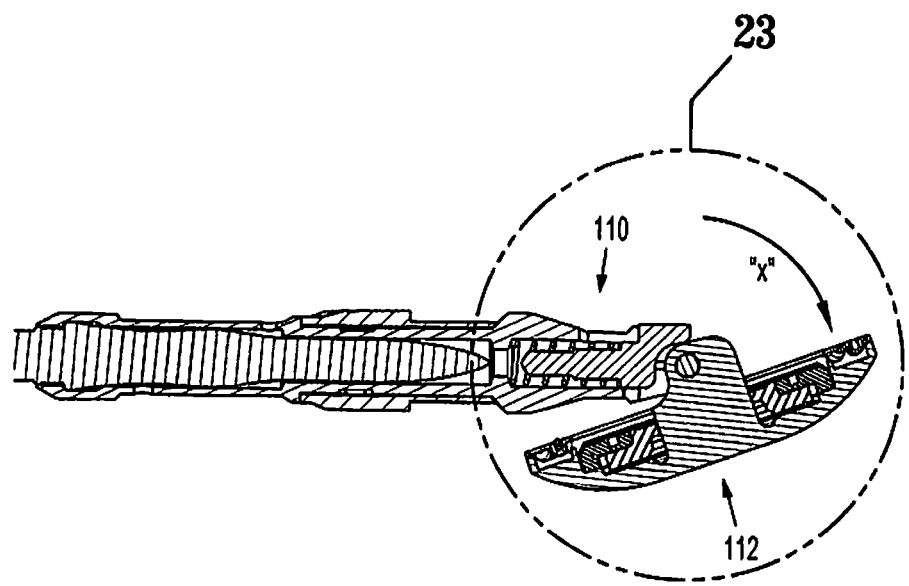
FIG. 22A is another cross-sectional side view of the anvil assembly of FIGS. 1-7 in a post-fired tilted position supported on an anvil retainer of the surgical instrument of FIG. 1
Figure 23:
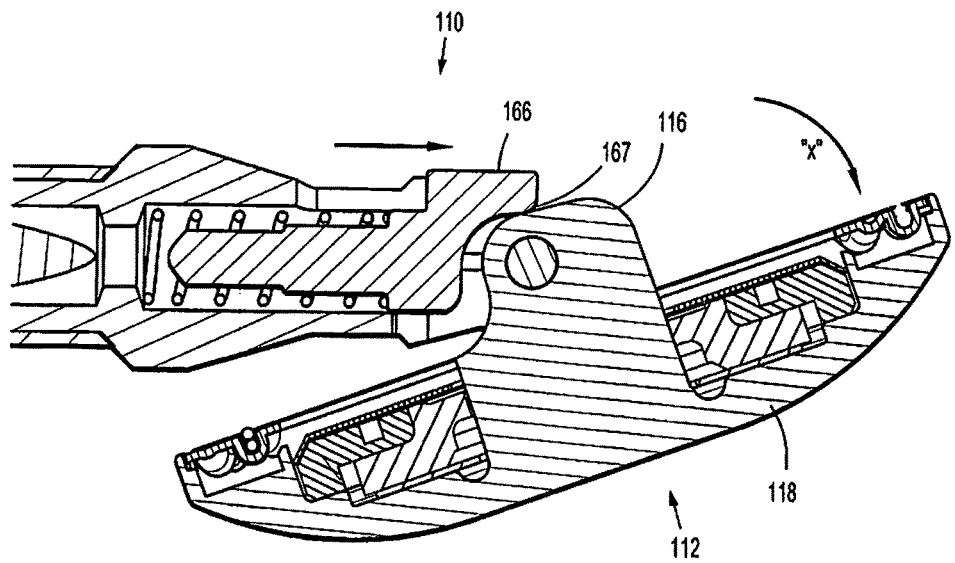
FIG. 23 is an enlarged view of the indicated area of detail shown in FIG. 22A.
Figure 24:
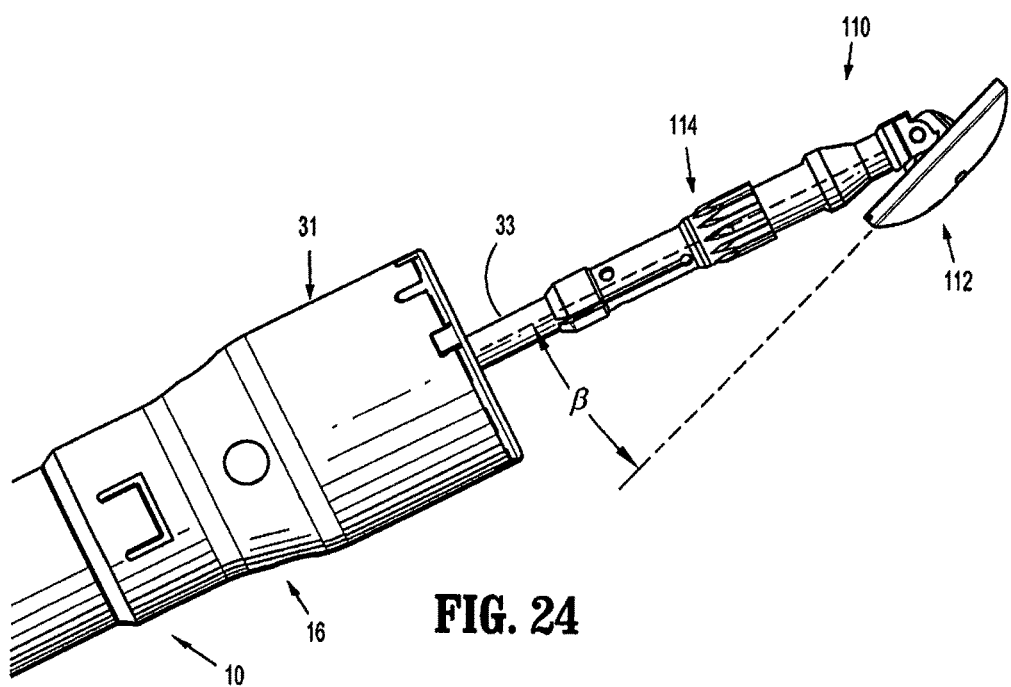
FIG. 24 is a side view of the anvil assembly of FIG. 22 supported on the anvil retainer of the surgical stapling device of FIG. 1.

The firing of surgical stapling device 10 causes a knife blade 33 thereof to engage cutting ring 122 to move cutting ring 122 and backup plate 120 into annular recess 136 of housing 118 of anvil head assembly 112. Arrows "W" in FIG. 19 indicate how cutting ring 122 and backup plate 120 move as a result of the firing of surgical stapling device 10. When such movement occurs, deformable tabs 127a of retainer 127 are deformed against backwall 118a of housing 118 and fingers 138 of backup member 120 move away from protrusions 152b of center rod 152. Further, inner periphery 120b of backup plate 120 moves past edge 126f of cam latch member 126 such that cam latch member 126 is urged to pivot about pivot member 162 in the direction indicated by arrow "X" in FIG. 21 by plunger 154 to a position in which body portion 126d is positioned in front of and engages backup plate 120. Engagement of plunger 154 with cam latch member 126 urges anvil head assembly 112 to a second tilted position (FIGS. 22 and 23). It is noted that anvil head assembly 112 will not immediately tilt upon firing of surgical stapling device 10 because, upon firing, anvil head assembly 112 is in an approximated position, i.e., the anvil head assembly 112 is in close alignment with shell assembly 31 of stapling device 10, and, therefore, does not provide room for head assembly 112 to pivot. As such, the anvil head assembly 112 will only begin to tilt when anvil assembly 110 and shell assembly 31 of surgical stapling device 10 are being unapproximated.

As anvil head assembly 112 pivots towards its forward or second tilted position, finger 166 of plunger 154 maintains surface 126e of cam latch member 126 in contact with backup plate 120 to prevent backup plate 120 from sticking to the knife blade as the knife blade is retracted. It is noted that curved surface 126e of cam latch member is configured to eliminate any gap and ensure contact between surface 126e of cam latch member 126 and backup plate 120 to hold backup plate 120 in place during and after the knife blade is retracted such that the cutting ring and backup plate assembly stay in their correct position during continued tilting of anvil assembly 112. Anvil assembly 110 is configured such that anvil head assembly tilts to a forward or second tilted position β degrees (FIG. 23) relative to center rod assembly 114. In one embodiment, anvil head assembly 112 is tilted about seventy degrees (70°) to its second tilted position such that the total pivoting movement of the anvil from the retracted or first tilted position to the forward or second tilted position is about one-hundred and forty degrees (140°). It should, however, be noted that the tilting of anvil head assembly 112 to other degrees is also contemplated.

Figure 25:
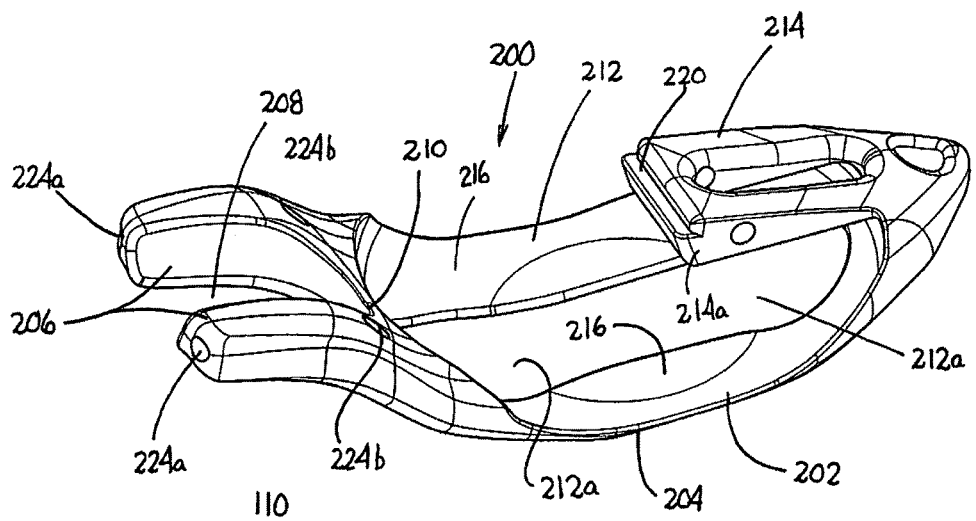
FIG. 25 is a side perspective view of a sled for use with the presently disclosed anvil assembly delivery system.
Figure 26:
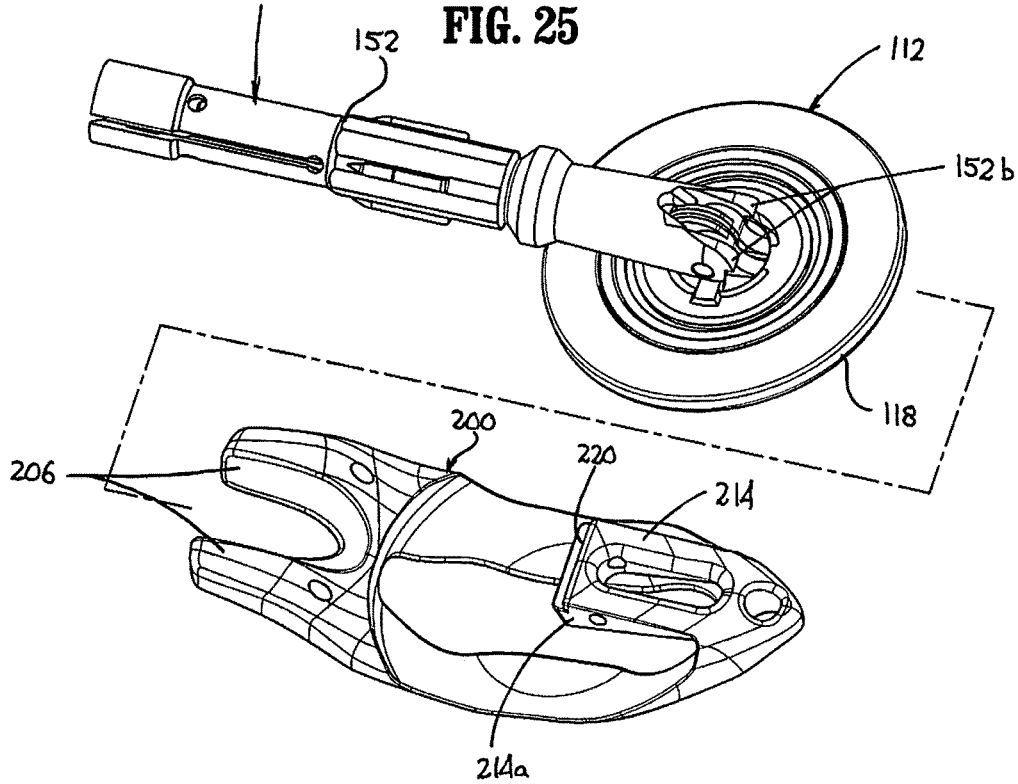
FIG. 26 is a side perspective view of the sled of the anvil assembly delivery system separated from the anvil assembly of FIG. 2.

FIG. 25 illustrates a sled 200 which is configured to be used in conjunction with the anvil assembly delivery system 50 described above to atraumatically deliver the anvil assembly 110 (FIG. 26) to a surgical site, e.g., the stomach "S$_t$" (FIG. 31), trans-orally. Referring also to FIG. 26, the sled 200 includes a body 202 having a smooth outer profile including a smoothly, curved top surface 204 (FIG. 30), a pair of spaced proximally extending arms 206 defining a recess 208, a bridge 210 interconnecting the arms 206, a concavity 212, and a retaining portion 214 extending proximally from the distal end of the body 202 at least partially over the concavity 212. The recess 208 is configured and dimensioned to receive the center rod 152 of the anvil assembly 110. The concavity 212 of body 202 includes a centrally located slot 212a and is configured and dimensioned to receive the anvil head assembly 112. The concavity 212 is defined by a surface 216 of the body 202 which supports a distal face 112a (FIG. 27) of the housing 118 of the anvil head assembly 112.

Figure 27:
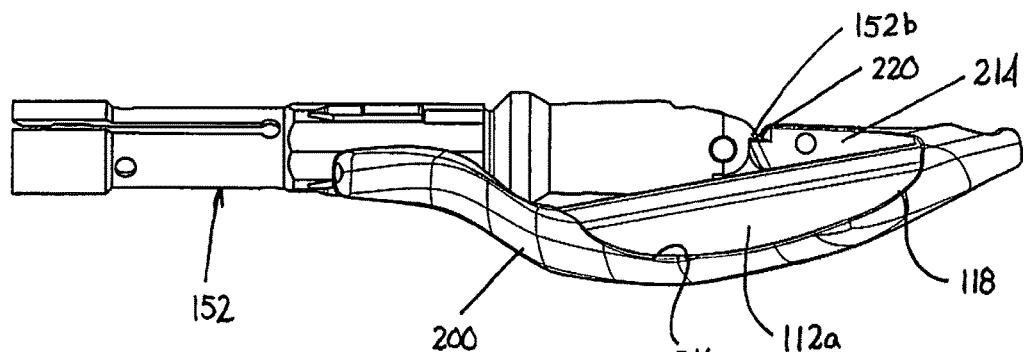
FIG. 27 is a side view of the sled and anvil assembly of FIG. 26 with the sled supported on the anvil assembly.
Figure 28:
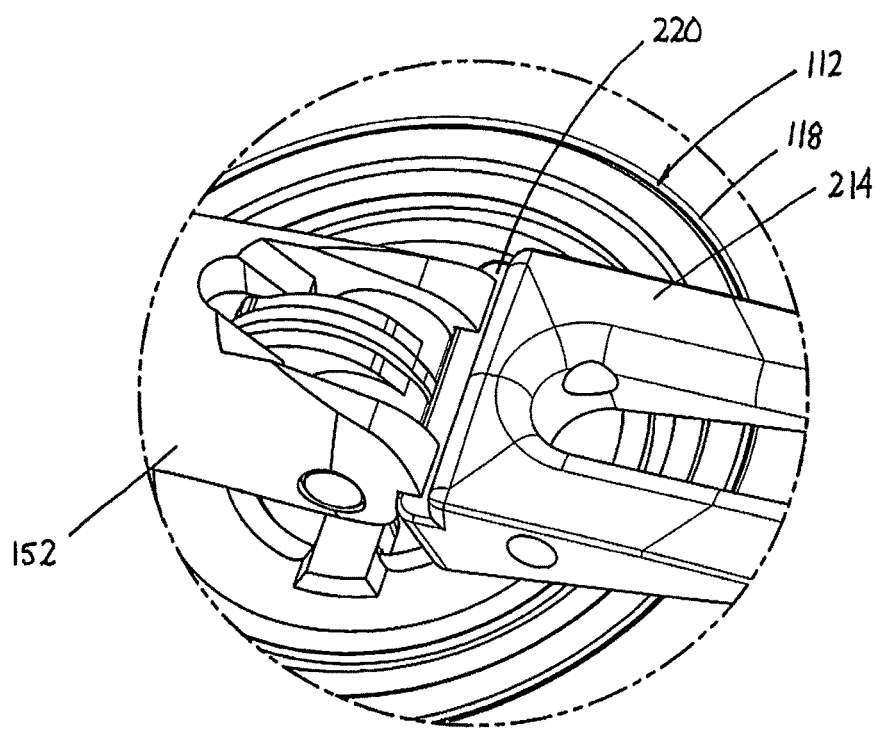
FIG. 28 is an enlarged perspective view of the indicated area of detail shown in FIG. 29.

Referring also to FIGS. 27-28, the retaining portion 214 of the sled 200 includes a stepped portion 220 at its distal end 214a. The stepped portion 220 is positioned to be fitted beneath the protrusions 152b which extend from the center rod 152 of the anvil assembly 110 when the sled 200 is supported on the anvil assembly 110. More particularly, when the housing 118 of the anvil head assembly 112 is positioned in the concavity 212 of the sled 200, the retaining portion 214 of the sled 200 extends over the housing 118 such that the stepped portion 220 of the retaining portion 214 is positioned under the protrusions 152b of the center rod 152.

Figure 29:
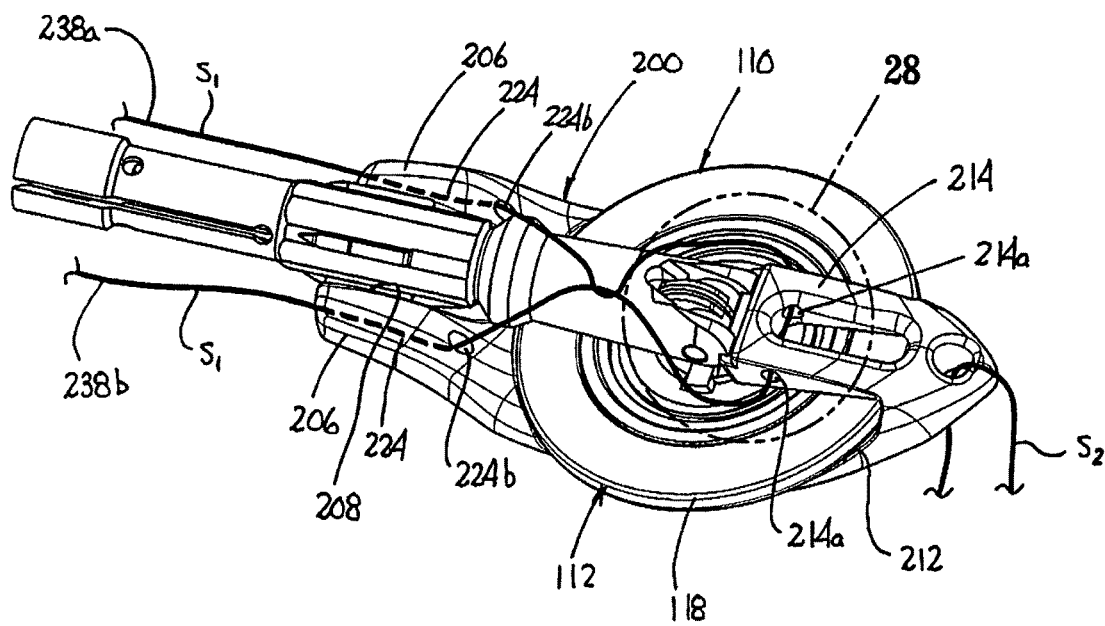
FIG. 29 is a bottom perspective view of the sled of FIG. 27 secured on the anvil assembly by a suture.

Referring to FIG. 29, each arm 206 of the sled 200 defines a first suture channel 224 having an inlet opening 224a (FIG. 25) and an outlet opening 224b. In addition, the retaining portion 214 of the sled 200 defines second suture channels 214a. Alternatively, a single second suture channel 214a can be defined in the retaining portion 214. When the housing 118 of the anvil head assembly 112 is positioned within the concavity 212 of the sled 200, the center rod 152 extends proximally from the concavity 212 over the bridge 210 and through the recess 208.

In this embodiment, to secure the sled 200 onto the anvil assembly 110, a first end 238a of the first suture "S$_1$" extends from the adapter 62 (FIG. 10) into an inlet opening 224a (FIG. 25) of one arm 206, through the suture channel 224 and out of the outlet opening 224b. From the outlet opening 224b, the suture "S$_1$" extends across the center rod 152 and into the suture channel 214a on an opposite side of the retaining portion 214. The suture "S$_1$" exits the other side of the suture channel 214a of the retaining portion 214 and again extends across the center rod 152 and into the outlet opening 224b of the other arm 206. The second end 238b of the suture "S$_1$" extends through the suture channel 224 of the other arm 206 back towards the adapter 62. With the suture "S$_1$" in the position described, the anvil center rod 152 is trapped between the suture "S$_1$" and the stepped portion 220 of the retaining portion 214 and the anvil head assembly 112 is trapped between the surface 216 of body 202 and retaining portion 214.

As discussed above with regard to FIGS. 9-13, when attaching the anvil assembly 110 to the flexible tube 52, each of the first and second ends of suture "S$_1$" is inserted through opening 55 formed in open end 52a of the flexible tube 52. Anvil head 112 is then rotated to a first tilted position while first and second ends of suture "S$_1$" are pulled through opening 55. First end 62a of adapter 62 is then inserted into open end 52a of flexible tube 52. The frictional contact between annular rings 64 of first end 62a of adapter 62 and an inner surface of flexible tube 52 secures adapter 62 to flexible tube 52 and prevents suture "S$_1$" from loosening to retain the anvil head assembly 112 in the first tilted position.

As shown in FIG. 29, the distal end of the sled 200 also defines a through bore 240 which receives the second suture "S$_2$". The second or retrieval suture "S$_2$" extends from the sled 200 in a direction opposite to the flexible tube 52 (FIG. 31) and can be grasped by a surgeon during delivery of the anvil assembly 110 to a surgical site to manipulate the anvil assembly 110. The "S$_2$" can also be grasped by a surgeon to retrieve the anvil assembly 112 after a surgical procedure is completed.

Figure 30:
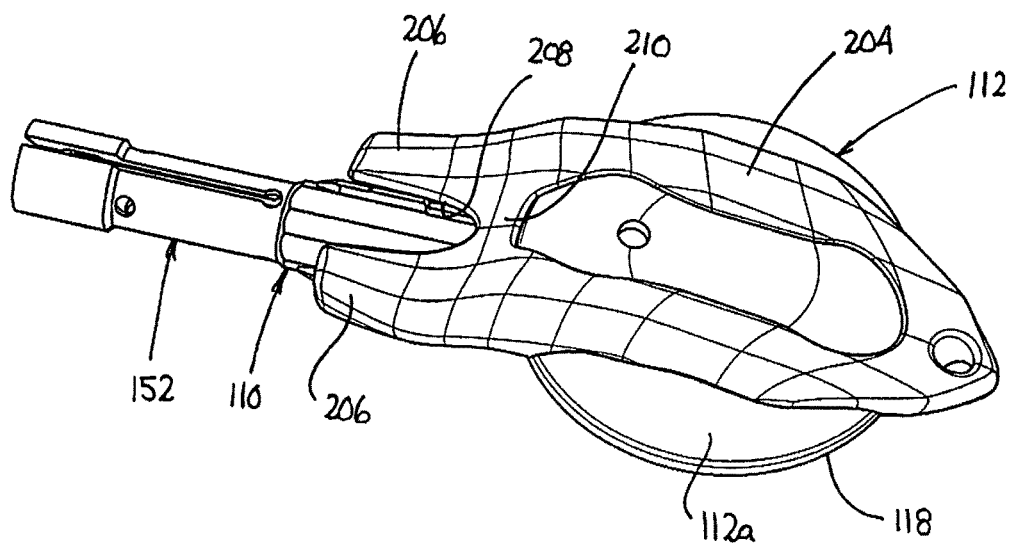
FIG. 30 is a top perspective view of the sled of FIG. 27 supported on the anvil assembly.
Figures 31, 31A:
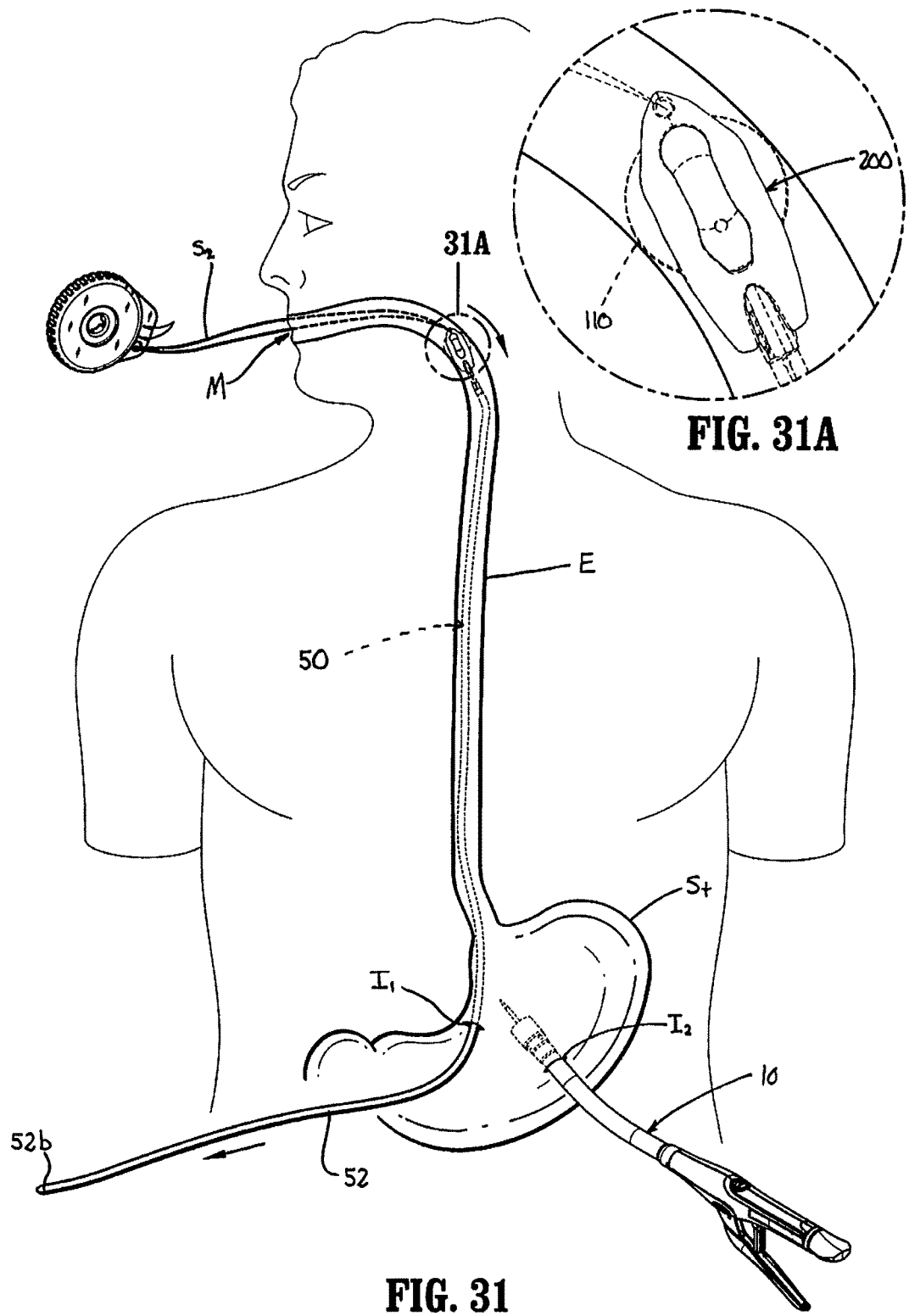
FIG. 31 is an illustration of anvil assembly delivery system of FIG. 15 including the sled shown in FIG. 24 as the anvil assembly is inserted trans-orally into a patient.
FIG. 31A is an enlarged view of the indicated area of detail shown in FIG. 31.

Referring to FIGS. 30 to 31A, a method for delivering anvil assembly 110 to a surgical site within a patient using the anvil delivery system 50 and the sled 200 will be described. In one method, anvil assembly 110 is provided in the first tilted position supported on anvil delivery system 50 and ready for delivery. Alternatively, a clinician secures anvil assembly 110 to anvil delivery system 50 as discussed above. Once anvil assembly 110 has been secured to flexible tube 52, the surgeon inserts closed end 52b of flexible tube 52 in the patient's mouth "M" and moves closed end 52b along with flexible tube 52 down through esophagus "E" to a surgical site, e.g., the stomach "St". As the anvil assembly 110 is drawn into the esophagus "E" with the flexible tube 52, the sled 200 and suture "S$_1$" holds the anvil head assembly 112 in the tilted position and the smooth outer profile of the sled 200 guides the anvil head assembly 112 atraumatically through the esophagus "E".

After the closed end 52b of the flexible tube 52 is inserted to the surgical site, the surgeon makes a first incision "I$_1$" at the surgical site (stomach "St" as shown) to access the closed end 52b of flexible tube 52. Then, the surgeon pulls the closed end 52b of flexible tube 52 through first incision "I$_1$". In some procedures, it may be beneficial to pull flexible tube 52 through incision "I$_1$" until center rod 152 of anvil assembly 110 advances through first incision "I$_1$". When anvil assembly 110 is properly positioned at the surgical site, the surgeon releases anvil delivery system 50 from anvil assembly 110 by cutting suture "S₁" and separating anvil assembly 110 from second end 62b of adapter 62 and the sled 200. Flexible tube 52 (with fitting 62) may then be pulled from the body through first incision "I₁" and the sled 200 can be removed from the body through the mouth "M" of the patient by pulling on the second suture "S₂". As discussed above with respect to anvil delivery system 50, severing of suture "S₁" permits the anvil head assembly 112 to rotate to a non-tilted position such that it can be attached to the distal head portion 16 of the surgical stapling device 10 (FIG. 1) through an incision "I₂". Alternatively, distal head portion 16 of surgical stapling device 10 may be received through first incision "I₁" once anvil delivery system 50 has been removed therefrom.

Figure 32:
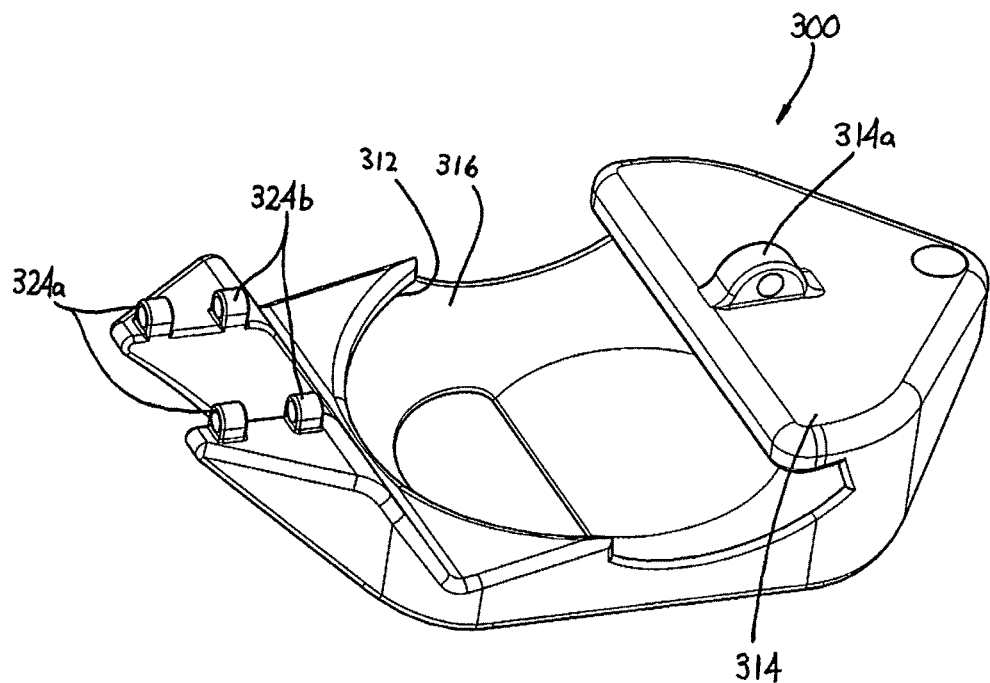
FIG. 32 is side perspective view of another embodiment of the sled shown in FIG. 24.
Figure 33:
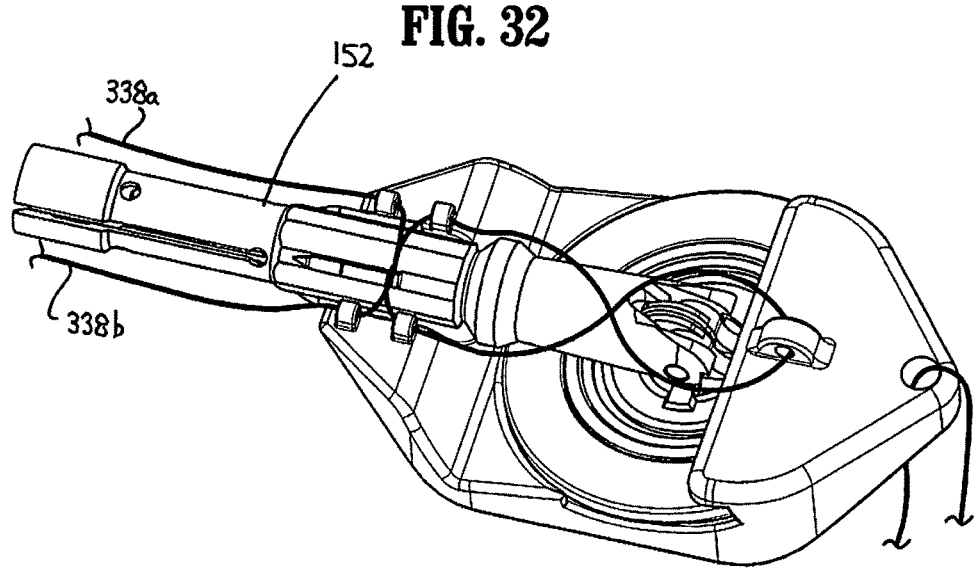
FIG. 33 is perspective view from the bottom of the sled shown in FIG. 32 secured to the anvil assembly of FIG. 2 by a suture.

FIGS. 32 and 33 illustrate a second embodiment of the presently disclosed sled shown generally as 300. Sled 300 is substantially similar to sled 200 but includes proximal and distal raised eyelets 324a and 324b which define the suture channels 224 and a raised eyelet 314a which defines the suture channel 214a on the retaining portion 314. In use, a first end 338a of the suture "S₁" extends from the adapter 62 (FIG. 10) and is inserted through one of the proximal raised eyelets 324a. The suture "S₁" extends from the proximal raised eyelet 324a across the center rod 152 and through one of the distal raised eyelets 324b. From the distal raised eyelet 324b, the suture "S₁" extends across the center rod 152 and into an opposite side of the raised eyelet 314a of the retaining portion 314 of the sled 300. The suture "S₁" extends through the raised eyelet 314a across the center rod 152 and through the other distal raised eyelet 324b. Thereafter, the second end 338b of the suture "S₁" extends back across the center rod 152 and into the other proximal raised eyelet 324a back to the adapter 62. The first and second ends of the suture "S₁" are connected to the adapter 62 as described above and will not be described in further detail herein. By providing spaced proximal and distal raised eyelets 324a and 324b, the suture "S₁" can be crossed over the center rod 152 between the raised eyelets 324a and 324b to better secure the sled 300 to the anvil assembly 110.

As discussed above with regard to sled 200, the sled 300 also defines a distal through bore 340 which receives a retrieval suture "S₂" to facilitate manipulation of the anvil assembly 110 during insertion of the anvil assembly 110 and retrieval of the anvil assembly 110 after use.

In an alternate embodiment of the presently disclosed sled, the concavity 312 of the sled defines an annular surface which is dimensioned to completely cover the anvil plate 124 (FIG. 4) including the staple pockets 132 (FIG. 3). By completely covering the anvil plate 124 and staple pockets 132 during insertion of the anvil assembly 110, the cleanliness of the anvil plate 124 and anvil pockets 132 can be maintained during trans-oral insertion of the anvil assembly to a surgical site. The sled is flexible. After the 51 suture is cut the sled is pulled/peeled off by the S2 suture. The head will start to tilt as soon as 51 is cut, but it will straighten a little as you pull S2 to remove the sled.

It will be understood that various modifications may be made to the embodiments disclosed herein. For example, the sled may assume a variety of configurations not shown herein so long which have a smooth outer profile to facilitate atraumatic insertion of the head assembly into a patient. Further, the recess defined between the arms 206 need not extend through the sled but rather may define only a groove. Therefore, the above description should not be construed as limiting, but merely as exemplifications of embodiments. Those skilled in the art will envision other modifications within the scope and spirit of the claims appended hereto.

What is claimed is:

1. A stapling anvil assembly comprising:
a flexible tube having a first closed end and a second end; and
a circular stapling anvil including a center rod and an anvil head, the anvil being secured to the second end of the flexible tube;
a sled having a body defining a concavity dimensioned to receive the anvil head and a recess dimensioned to receive a center rod of the anvil, the body having a smooth outer profile and further defining a first suture channel on each side of the recess to facilitate securement of the body to the anvil; and
a first suture positioned through the first suture channels of the body to secure the anvil head within the concavity of the body.

2. The stapling anvil assembly according to claim 1, wherein the body of the sled includes a retaining portion which extends at least partially over the concavity to retain the anvil head assembly within the concavity.

3. The stapling anvil assembly according to claim 2, wherein the retaining portion of the body defines a second suture channel, the second suture channel receiving the first suture to facilitate securement of the anvil head within the concavity of the body of the sled.

4. The stapling anvil assembly according to claim 1, wherein the sled defines a through bore, and further including a retrieval suture extending through the through bore.

5. The stapling anvil assembly according to claim 1, wherein the anvil head is pivotally secured to the center rod, the anvil head being pivotal from a first tilted position to a non-tilted operative position.

6. The stapling anvil assembly according to claim 1, further including an adapter, the adapter connecting the flexible tube to the center rod of the anvil.

7. The stapling anvil assembly according to claim 6, wherein the first suture is secured to the adapter to retain the anvil head in the first tilted position.

* * * * *